(12) United States Patent
Giftakis et al.

(10) Patent No.: US 10,632,311 B2
(45) Date of Patent: *Apr. 28, 2020

(54) BRAIN STIMULATION RESPONSE PROFILING

(71) Applicant: Medtronic, Inc., Minneapolis, MN (US)

(72) Inventors: Jonathon E. Giftakis, Maple Grove, MN (US); Paul H. Stypulkowski, North Oaks, MN (US); Timothy J. Denison, Minneapolis, MN (US); Scott R. Stanslaski, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 229 days.

This patent is subject to a terminal disclaimer.

(21) Appl. No.: 15/646,934

(22) Filed: Jul. 11, 2017

(65) Prior Publication Data
US 2017/0304629 A1 Oct. 26, 2017

Related U.S. Application Data

(63) Continuation of application No. 14/194,026, filed on Feb. 28, 2014, now Pat. No. 9,724,517, which is a (Continued)

(51) Int. Cl.
*A61N 1/36* (2006.01)
*A61N 1/372* (2006.01)
*A61N 1/05* (2006.01)

(52) U.S. Cl.
CPC ....... *A61N 1/36146* (2013.01); *A61N 1/3615* (2013.01); *A61N 1/36064* (2013.01);
(Continued)

(58) Field of Classification Search
CPC .............. A61N 1/36146; A61N 1/3615; A61N 1/36167; A61N 1/36139; A61N 1/36082;
(Continued)

(56) References Cited

U.S. PATENT DOCUMENTS 6,161,045 A 12/2000 Fischell et al.
6,463,328 B1 10/2002 John
(Continued)

FOREIGN PATENT DOCUMENTS

WO 2002038031 A2 5/2002

OTHER PUBLICATIONS

Duffau, "Contribution of Cortical and Subcortical Electrostimulation in Brain Glioma Surgery: Methodological and Functional Considerations," Clinical Neurophysiology, vol. 27, Dec. 2007, pp. 373-382.
(Continued)

*Primary Examiner* — Michael W Kahelin
(74) *Attorney, Agent, or Firm* — Shumaker & Sieffert, P.A.

(57) ABSTRACT

Various embodiments concern delivering electrical stimulation to the brain at a plurality of different levels of a stimulation parameter and sensing a bioelectrical response of the brain to delivery of the electrical stimulation for each of the plurality of different levels of the stimulation parameter. A suppression window of the stimulation parameter can be identified as having a suppression threshold as a lower boundary and an after-discharge threshold as an upper boundary based on the sensed bioelectrical responses. A therapy level of the stimulation parameter can be set for therapy delivery based on the suppression window. The therapy level of the stimulation parameter may be set closer to the suppression threshold than the after-discharge threshold within the suppression window. Data for hippocampal
(Continued)

stimulation demonstrating a suppression window is presented.

26 Claims, 11 Drawing Sheets

Related U.S. Application Data continuation of application No. 13/766,006, filed on Feb. 13, 2013, now Pat. No. 8,706,237.

(60) Provisional application No. 61/732,016, filed on Nov. 30, 2012, provisional application No. 61/600,697, filed on Feb. 19, 2012.

(52) U.S. Cl.
CPC ..... *A61N 1/36067* (2013.01); *A61N 1/36082* (2013.01); *A61N 1/36139* (2013.01); *A61N 1/36167* (2013.01); *A61N 1/372* (2013.01); *A61N 1/0534* (2013.01)

(58) Field of Classification Search
CPC ............ A61N 1/36064; A61N 1/36067; A61N 1/372; A61N 1/0534
See application file for complete search history.

(56) References Cited

U.S. PATENT DOCUMENTS

| 6,690,974 | B2 | 2/2004 | Archer et al. |
| 6,882,881 | B1 | 4/2005 | Lesser et al. |
| 7,089,059 | B1 | 8/2006 | Pless |
| 7,228,171 | B2 | 6/2007 | Lesser et al. |
| 7,551,956 | B2 | 6/2009 | Osorio et al. |
| 7,561,918 | B2 | 7/2009 | Armstrong et al. |
| 7,620,456 | B2 | 11/2009 | Gliner et al. |
| 8,706,237 | B2 | 4/2014 | Giftakis et al. |
| 9,724,517 | B2 | 8/2017 | Giftakis et al. |
| 2002/0072770 | A1 | 6/2002 | Pless |
| 2004/0019370 | A1 | 1/2004 | Gliner |
| 2005/0228461 | A1 | 10/2005 | Osorio et al. |
| 2007/0055320 | A1 | 3/2007 | Weinand |
| 2007/0167991 | A1 | 7/2007 | Dilorenzo |
| 2010/0100153 | A1 | 4/2010 | Carlson et al. |
| 2010/0280334 | A1 | 11/2010 | Carlson et al. |
| 2010/0280335 | A1 | 11/2010 | Carlson et al. |
| 2013/0053722 | A1 | 2/2013 | Carlson et al. |

OTHER PUBLICATIONS

Rajdev, et al., "Effect of Stimulus Parameters in the Treatment of Seizures by Electrical Stimulation in the Kainate Animal Model," International Journal of Neural Systems, vol. 21, No. 2, Mar. 2011, pp. 151-162.

International Search Report and Written Opinion from International Application No. PCT/US2013/026024, dated May 7, 2013, 11 pp.

International Preliminary Report on Patentability from International Application No. PCT/US2013/026024, dated Aug. 19, 2014, 7 pp.

Notice of Allowance from U.S. Appl. No. 13/766,006, dated Dec. 6, 2013, 12 pp.

Prosecution History from U.S. Appl. No. 14/194,026, dated Dec. 9, 2015 through Apr. 5, 2017, 118 pp.

Communication pursuant to Rules 161(1) and 162 EPC from European Application No. 13706379.8, dated Nov. 24, 2014, 2 pp.

Response to Communication pursuant to Rules 161(1) and 162 EPC dated Nov. 24, 2014, from European Application No. 13706379.8, filed on May 4, 2015, 7 pp.

Response to Examination Report dated Jan. 17, 2018, from counterpart European Application No. 13706379.8, filed Jul. 26, 2018, 6 pp.

Examination Report from counterpart European Application No. 13706379.8, dated Jan. 17, 2018, 6 pp.

200

BRAIN STIMULATION RESPONSE PROFILING

This application is a continuation of U.S. patent application Ser. No. 14/194,026, filed on Feb. 28, 2014, now U.S. Pat. No. 9,724,517, which is a continuation of U.S. patent application Ser. No. 13/766,006, filed on Feb. 13, 2013, now U.S. Pat. No. 8,706,237, which claims the benefit of U.S. Provisional Patent Application Ser. No. 61/600,697, filed Feb. 19, 2012, and U.S. Provisional Patent Application Ser. No. 61/732,016, filed Nov. 30, 2012. The entire content of each of these applications is incorporated herein by reference.

TECHNICAL FIELD

The disclosure relates to medical devices and, more particularly, to medical devices for therapeutic brain stimulation.

BACKGROUND

Implantable medical devices, such as electrical stimulators or therapeutic agent delivery devices, may be used in different therapeutic applications, such as deep brain stimulation (DBS) or the delivery of pharmaceutical agent to a target tissue site within a patient. A medical device may be used to deliver therapy to a patient to treat a variety of symptoms or patient conditions such as chronic pain, tremor, Parkinson's disease, other types of movement disorders, seizure disorders (e.g., epilepsy), obesity or mood disorders. In some therapy systems, an external or implantable electrical stimulator delivers electrical therapy to a target tissue site within a patient with the aid of one or more implanted electrodes, which may be deployed by medical leads or on a housing of the stimulator. In addition to or instead of electrical stimulation therapy, a medical device may deliver a therapeutic agent to a target tissue site within a patient with the aid of one or more fluid delivery elements, such as a catheter or a therapeutic agent eluting patch.

SUMMARY

Various anti-seizure therapies and other therapies can attempt to suppress brain activity to reduce seizures or produce another therapeutic effect. Stimulation can cause episodes of after-discharge. The chronic triggering of after-discharge events is not regarded as a therapy goal. Rather, suppression or other change in brain state without an after-discharge represents a preferred effect for chronic therapy delivery. Data is shown from hippocampal stimulation showing that a suppression effect without an after-discharge was produced with a pulse parameter level above a parameter level that failed to suppress bioelectrical activity but below a pulse parameter level that caused an after-discharge. The data demonstrates a limited range for a pulse parameter in producing a preferred therapeutic effect. As such, a preferred stimulation parameter level is bounded by the thresholds for producing suppression and after-discharge. Specifically, a narrow parameter window for various types of stimulation therapy is bounded by a suppression threshold on the lower end and an after-discharge threshold on the upper end. The narrow window for therapy delivery can be profiled and used to set stimulation outputs for therapy delivery.

Various embodiments concern delivering electrical stimulation to the brain at a plurality of different levels of a stimulation parameter and sensing a bioelectrical response of the brain to delivery of the electrical stimulation for each of the plurality of different levels of the stimulation parameter. A suppression window of the stimulation parameter can be identified as having a suppression threshold as a lower boundary and an after-discharge threshold as an upper boundary based on the sensed bioelectrical responses. A therapy level of the stimulation parameter can be set for therapy delivery based on the suppression window. The therapy level of the stimulation parameter may be set closer to the suppression threshold than the after-discharge threshold within the suppression window. Data for hippocampal stimulation demonstrating a suppression window is presented. Various embodiments concern implantable medical devices for managing therapy delivery consistent with the techniques disclosure herein.

DETAILED DESCRIPTION

Figure 1:
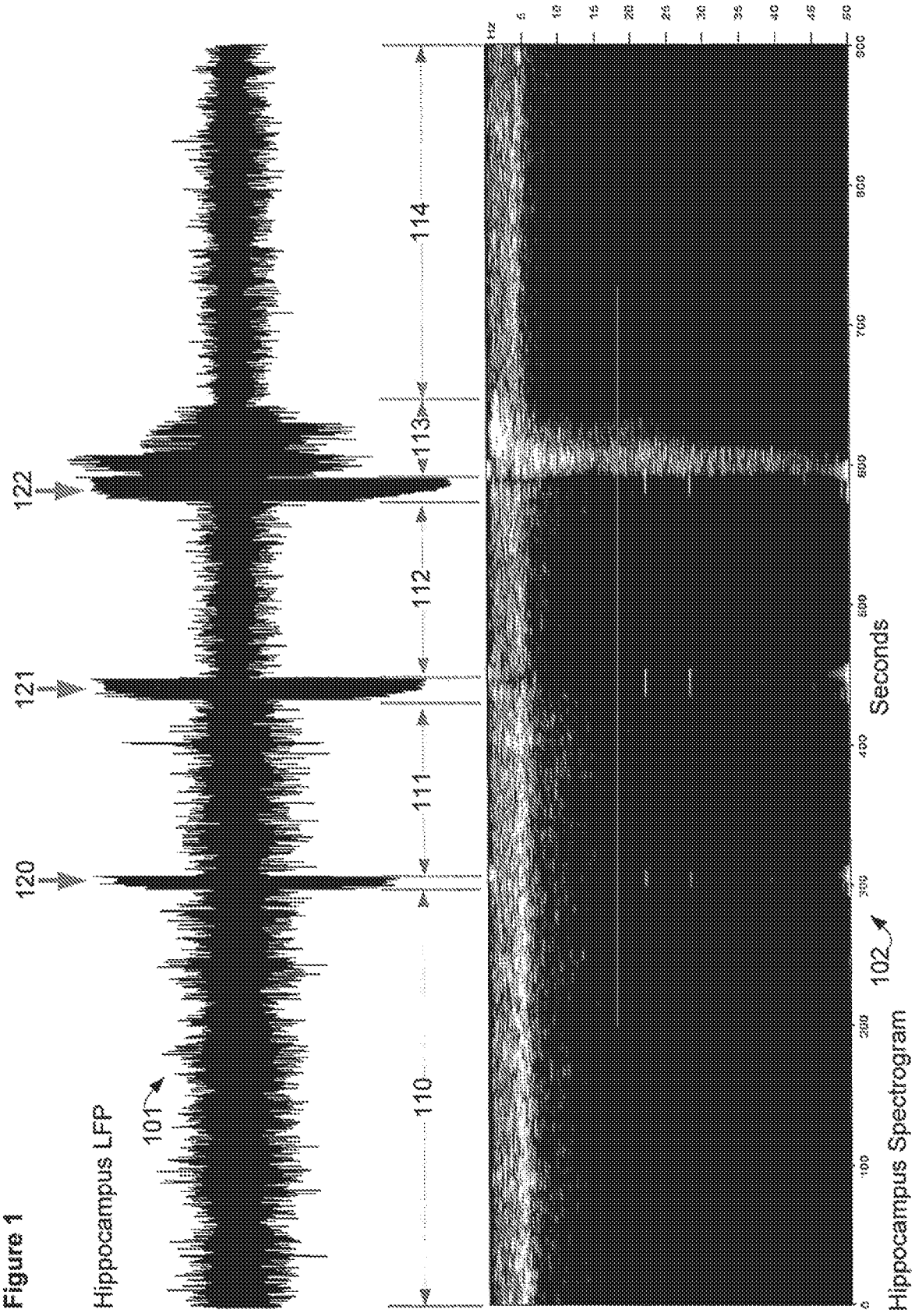
FIG. 1 shows data plots of bioelectrical response information from electrical brain stimulation.

Epilepsy and other conditions can be characterized by inappropriate bioelectrical brain activity within one or more brain structures. For example, some seizures associated with temporal lobe epilepsy can arise in the hippocampus of the brain. Accordingly, for at least some patients, reducing the bioelectrical activity level within the hippocampus may reduce problematic cortical activity and may be desirable for managing a seizure disorder. The reduced bioelectrical activity level within the hippocampus may help mitigate symptoms of the seizure disorder, such as by lowering the likelihood of the occurrence of a seizure, reducing the severity or duration of seizures, and/or reducing the frequency of seizures.

Deep brain stimulation is one option for therapeutically addressing a seizure disorder by lowering the activity within the hippocampus or other brain area. For example, a lead can be implanted with one or more electrodes contacting the hippocampus or other brain area targeted for stimulation therapy. Electrical stimulation delivered from the one or more electrodes can change the intrinsic bioelectrical electrical activity of the hippocampus or other targeted brain area.

One of the challenges of hippocampal deep brain stimulation for epilepsy is selection of stimulation parameters for best treatment. Currently, continuous low-voltage stimulation can be used for therapy. In some cases, therapeutic electrical stimulation of the hippocampus can be delivered at a lower energy level relative to therapeutic electrical stimulation of the some other brain targets because of the sensitivity of the hippocampus to stimulation. The paradox is that stimulation of the hippocampus can cause after-discharges, which are brief seizure-like episodes of bioelectrical activity that occur during and/or immediately following electrical stimulation.

Hippocampal deep brain stimulation is preferably managed for some patients to maintain the intensity of the therapy at a level that therapeutically addresses the seizure disorder while not causing unintended brain events. For example, some stimulation parameters may fail to lower bioelectrical activity or otherwise therapeutically address the seizure condition while some other stimulation parameters may be associated with unintended side effects. As mentioned above, electrical stimulation at some energy levels can cause an after-discharge in the hippocampus.

Sensing bioelectrical activity in the brain is a useful tool for calibrating electrical stimulation parameters. For example, the bioelectrical activity of the hippocampus or other brain area can be monitored in real-time to provide feedback on the level of reduction of brain activity contributing to the seizure disorder and further on the occurrence of any unwanted stimulation side effects.

This disclosure presents, among other things, a demonstration of different therapy levels in an ovine model and algorithms for therapy management. Various embodiments are presented for identifying a window of a stimulation parameter between a minimum therapeutic threshold and a minimum threshold for unwanted provocation from the stimulation. Various embodiments concern monitoring bioelectrical activity to set stimulation therapy parameter levels to maintain suppression of bioelectrical activity or otherwise cause a change in a brain state while avoiding after-discharge events. The target locations for sensing and/or stimulation can be the hippocampus, as demonstrated herein, or other targets within the brain. These and other aspects of therapy management are discussed herein.

As mentioned previously, the hippocampus is an interesting target in the brain for because of the role of the hippocampus in various seizure disorders. Tests were done in an ovine model to understand the sensing capabilities of an implantable brain stimulator device (an ACTIVA™ PC implantable neurostimulator modified for sensing, made by MEDTRONIC™, Minneapolis, Minn., USA). Monitoring of bioelectrical activity was benefited by the ability to sense bioelectrical activity and detect brain events while electrical stimulation was being delivered. Sensing of brain signals and detecting brain events in the presence of electrical stimulation is discussed in commonly assigned U.S. application Ser. No. 13/589,270 filed on Aug. 20, 2012, by Carlson et al., titled METHOD AND APPARATUS FOR DETECTING A BIOMARKER IN THE PRESENCE OF ELECTRICAL STIMULATION, which is incorporated by reference herein in its entirety.

Preceding the tests, animals were anesthetized for surgery and 1.5 T MRIs collected. Unilateral anterior thalamic and hippocampal DBS leads were implanted using a frameless stereotactic system, and connected to the modified neurostimulator. Trajectories for unilateral thalamic and hippocampal DBS leads were calculated based upon gross anatomic descriptions of the ovine brain. The implanted system allowed for stimulation and recording from both leads. In particular, the implanted system allowed for sensing and stimulation of both the hippocampus and anterior nucleus structures. Evoked potentials and local field potential (LFP) signals were recorded by the implanted device (422 Hz sampling rate; 0.5 Hz HP, 100 Hz LP filters), downloaded, and analyzed off-line. The test results discussed herein principally concern the direct stimulation and monitoring of the hippocampus by a stimulation electrode in contact with the hippocampus, however the concepts discussed herein could be applicable to indirect stimulation and/or monitoring of the hippocampus (e.g., by an electrode within the brain but remote from the hippocampus, such as an electrode in a brain area networked to the hippocampus) as well as direct and/or indirect sensing and stimulation of other brain structures.

FIG. 1 shows a hippocampus LFP time domain signal 101 (upper chart) recorded from a lead implanted in the hippocampus. The signal 101 was recorded over a period of approximately 15 minutes during an awake phase for the animal subject. The lower chart of FIG. 1 shows a corresponding spectrogram 102 for the LFP signal 101 over the same time period.

Several notable time periods are indicated on FIG. 1. No stimulation was delivered during first time period 110. During the first time period 110, a steady level of intrinsic bioelectrical activity of the brain can be seen in both the LFP signal 101 and the spectrogram 102. From this steady brain activity level over the first time period 110, a baseline amount of bioelectrical activity can be established, the baseline reflecting the amount of brain activity present when the hippocampus is unaffected by stimulation. As will be shown herein, the establishment of a baseline can be useful as a reference for comparing bioelectrical brain activity levels affected by stimulation to assess the effect of the stimulation. The root mean square (RMS) of the LFP signal 101 and/or the spectral energy of the spectrogram 102 for the time period 110 can be used to measure the baseline bioelectrical activity level, among other techniques.

During the period of collection of the LFP signal 101, three groups of stimulation pulses were delivered to the hippocampus through the hippocampal lead in three different bursts of stimulation. The pulses within each group were delivered at 50 Hz. A different pulse amplitude was used for the pulses of each group of stimulation pulses. The first group 120 of stimulation pulses had an amplitude of 0.5 volts. The dominant artifact of the first group 120 of stimulation pulses is reflected in both the LFP signal 101 and the spectrogram 102 at approximately 300 seconds.

The second time period 111 immediately follows the delivery of the first group 120 of stimulation pulses. No stimulation was delivered during the second time period 111. As shown in both the LFP signal 101 and the spectrogram 102, the level of hippocampal activity during the second time period 111 is essentially the same as the level of hippocampal activity during first time period 110 associated with no stimulation. As such, hippocampal brain activity was unchanged from the unstimulated baseline level following the first group of 0.5 volt stimulation pulses and the amplitude of the first group 120 of stimulation pulses of the test was sub-threshold for any effect.

At about 440 seconds into the test, a second group 121 of stimulation pulses was delivered at 50 Hz and 0.9 volts. As with the other groups of pulses, the dominant artifact of the second group 121 of stimulation pulses is shown by both the LFP signal 101 and the spectrogram 102. The third time period 112 immediately follows the second group 121 of stimulation pulses. No stimulation was delivered during the third time period 112. As shown in both the LFP signal 101 and the spectrogram 102, the level of hippocampal activity during the third time period 112 (i.e. following the second group 121 of stimulation pulses) was lower relative to the first time period 110 and the second time period 111. In particular, following the delivery of higher amplitude stimulation pulses (the second group 121 at 0.9 volts), the hippocampal LFP activity decreased in amplitude and across all measured frequencies relative to baseline hippocampal LFP activity unassociated with stimulated (first time period 110) and relative to hippocampal LFP activity associated with lower amplitude stimulation (the first group 120 at 0.5 volts immediately preceding second time period 111). Based on this pattern, and as discussed further herein, it is concluded that the second group 121 of stimulation pulses suppressed the hippocampal LFP activity for some time following the stimulation. In this way, the increase in stimulation amplitude from 0.5 to 0.9 volts crossed a suppression threshold, where the lower amplitude first group 120 of stimulation pulses failed to suppress the bioelectrical activity of the hippocampus but the high amplitude second group 121 of stimulation pulses resulted in an immediate suppression of LFP activity in the hippocampus.

It is noted that the suppression of the third time period 112 is characterized by a consistent reduction in the amplitude of the LFP signal 101 and a consistent reduction in the spectral energy across all measured frequencies of the spectrogram 102 relative to the baseline levels of the first time period 110, which are both sustained for over a minute. These characteristics can be used for the detection of the suppression effect, as discussed herein.

The data of FIG. 1 further demonstrates the test results from increasing pulse amplitude and recording the bioelectrical response. A third group 122 of stimulation pulses was delivered at about 580 seconds. The pulse amplitude of the third group 122 of stimulation pulses was 1.3 volts. The fourth time period 113 immediately follows the third group 122 of stimulation pulses. No stimulation was delivered during the fourth time period 113. As shown in both the LFP signal 101 and the spectrogram 102 during the fourth time period 113, a significant increase in hippocampal bioelectrical activity was recorded following the third group 122 of stimulation pulses relative to the baseline bioelectrical activity of the time period 110, the bioelectrical activity of second time period 111 associated with ineffectual stimulation, and suppressed bioelectrical activity level of the third time period 112. The bioelectrical response pattern of the fourth time period 113 is consistent with an after-discharge episode, which can be detected as an epileptiform-like surge of neurological activity in response to stimulation. As shown in FIG. 1, the after-discharge is characterized by a sharp increase in the amplitude of the LFP signal 101 and an increase in the spectral energy across all measured frequencies of the spectrogram 102, which are both sustained for over ten seconds. These characteristics can be used for detection of after-discharge episodes, as discussed herein.

The after-discharge event of the fourth time period 113 lasts for about thirty seconds, during which time the animal exhibited a clinical orienting behavioral response. The significantly increased bioelectrical activity of the after-discharge event subsided by the fifth time period 114. The fifth time period 114 shows hippocampal bioelectrical activity below the baseline level of the first time period 110. The decreased hippocampal activity during fifth time period 114 is believed to be similar to postictal quieting and accordingly is of a different nature than the suppression of the third time period 112. Following the after-discharge episode of the fourth time period 113, bioelectrical brain activity remained suppressed for the fifth time period 114.

The tests indicate the appearance of local hippocampus suppression at stimulus levels just below the threshold for after-discharge generation. This inhibition of local activity persisted for some time after the stimulation ended, and then dissipated as LFP activity returned toward baseline. This suppression was reproducible and could be obtained within a narrow window of stimulation parameter levels that were supra-threshold for the suppression effect, but sub-threshold for after-discharge generation. The demonstration of prolonged, local hippocampus suppression at relatively low stimulus levels in the awake animal just below the after-discharge threshold provides a basis for stimulation level titration to treat temporal lobe epilepsy, among other conditions, as further discussed herein.

The tests demonstrates that along an increasing stimulation energy spectrum, the range of stimulation outputs that produce suppression in the hippocampus is just below the after-discharge threshold, as shown in FIG. 1. As such, a scan of an increasing or decreasing energy parameter (e.g., pulse amplitude, width, current, and/or frequency) can reveal a minimum suppression threshold (below which significant suppression is not observed), a stimulation parameter window within which stimulation parameters suppress bioelectrical activity, and an after-discharge threshold, above which after-discharges are provoked by stimulation.

Various anti-seizure therapies and other therapies can attempt to suppress brain activity to reduce seizures. However, the chronic triggering of after-discharge events is not regarded as a therapy goal. Rather, suppression or other change in brain state without an after-discharge, as demonstrated with the second group 121 of stimulation pulses and the subsequent third time period 112 of suppressed bioelectrical activity, represents a preferred effect for chronic therapy delivery. Being that the suppression effect without an after-discharge was produced with a pulse parameter level above the parameter level that failed to suppress bioelectrical activity (i.e. the pulse amplitude of the first group 120) but below a pulse parameter level that caused an after-discharge (i.e. the pulse amplitude of the third group 122), the test of FIG. 1 demonstrates a limited range for a pulse parameter in producing a preferred therapeutic effect. The inventors have thus discovered, among other things, that a preferred stimulation parameter level is bounded by the thresholds for producing suppression and after-discharge. Specifically, a narrow window for therapy delivery is bounded by a suppression threshold on the lower end and an after-discharge threshold on the upper end.

Figure 2:
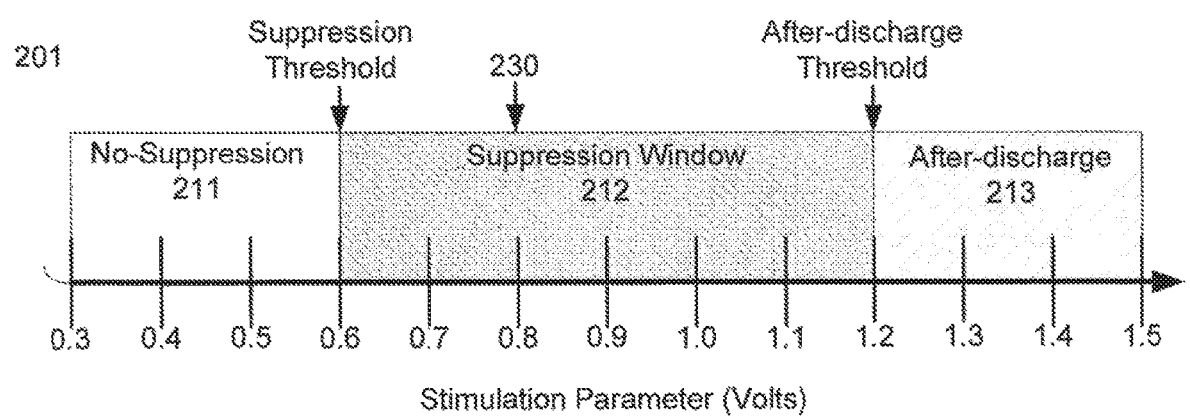
FIG. 2 is a diagram illustrating an example bioelectrical response profile.

The narrow window for therapy delivery can be profiled and used to set stimulation outputs for therapy delivery. FIG. 2 shows a profile of the data from the test of FIG. 1. It is noted that the interpolation of FIG. 2 makes guesses at the finer suppression and after-discharge threshold levels for the sake of discussion herein, but greater sampling could further pinpoint these thresholds as needed, depending on the resolution desired. FIG. 2 illustrates a stimulation parameter spectrum 201 measured in volts. The parameter spectrum 201 has one-tenth volt increments.

As demonstrated in the test of FIG. 1, different stimulation parameter levels produce different bioelectrical responses. Pulse amplitudes below the suppression threshold fail to suppression brain activity to an acceptable degree. The no-suppression window 211 of FIG. 2 accordingly spans from zero volts to 0.6 volts, up to a suppression threshold.

The suppression window 212 is adjacent to each of the no-suppression window 211 and the after-discharge window 213. As such, the suppression window 212 is defined by the suppression threshold and the after-discharge threshold. Stimulation using a parameter level within the suppression window 212 will cause the desired suppression effect without provoking an unwanted after-discharge event. Stimulation using a parameter level within the after-discharge window 213 will provoke an after-discharge event. The after-discharge window 213 may extend above 1.5 volts but exploring bioelectrical responses above the after-discharge window 213 is outside of the scope of this disclosure.

A chart identical or similar to that of FIG. 2 can be generated and displayed to profile the responses of a patient along a stimulation parameter spectrum. This information can be useful to a clinician for understanding the unique response profile of a particular patient. A parameter level for therapy delivery may be set based on the profile. For example, a stimulation parameter setting 230 may be selected within the suppression window 212 for therapy delivery. As shown in FIG. 2, the stimulation parameter setting 230 is weighted to be closer to the suppression threshold than to the after-discharge threshold (by a ratio of 1/3) along the stimulation parameter spectrum 201. Selecting a therapy output weighted closer to the suppression threshold within the suppression window may provide a stimulation output that reliably produces the suppression therapeutic effect while minimizing energy use and the likelihood of unintended stimulation. It is noted that the techniques discussed in connection with FIGS. 1 and 2 can be implemented by control circuitry of a medical device to automatically, among other things, identify a suppression window and/or set a parameter level for therapy delivery.

FIG. 2 shows that the zones of no-suppression 211, suppression window 212, and after-discharge 213 are contiguous along a stimulation parameter spectrum. As such, a scan of a stimulation parameter (e.g., pulse amplitude) along the stimulation parameter spectrum can identify the zones, thresholds, and the suppression window for setting therapy settings. Scans along a stimulation parameter spectrum will further be discussed in association with FIGS. 3 and 4.

Figure 3:
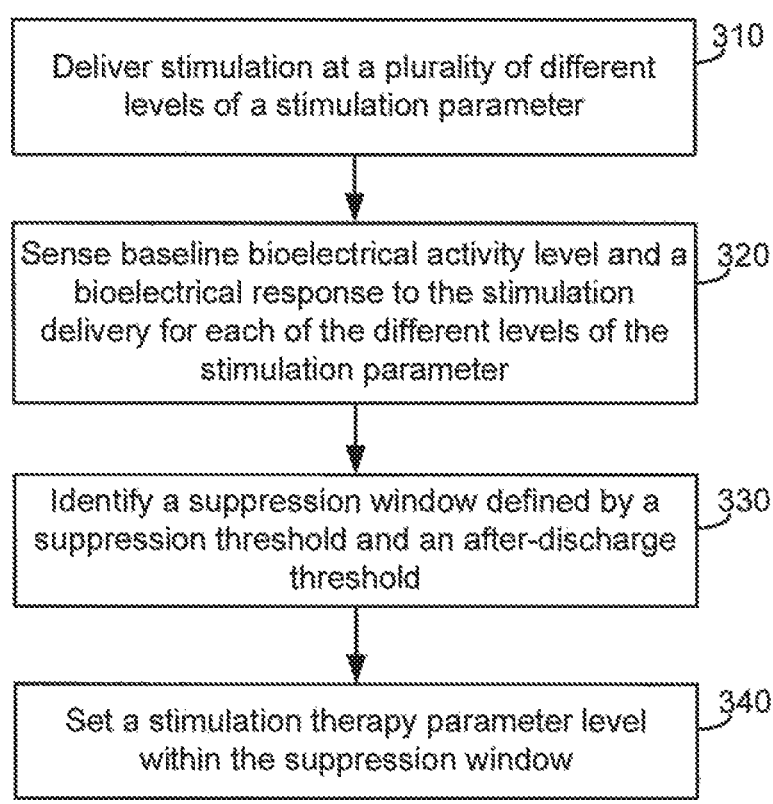
FIG. 3 is a flowchart for identifying a suppression window and setting a stimulation parameter.

FIG. 3 shows a flowchart of a method 300 for determining one or more stimulation parameters. The stimulation parameters could be used for the treatment of epilepsy, e.g., treating seizures associated with temporal lobe epilepsy with hippocampal stimulation. However, the techniques of FIG. 3 could be applied to various other brain areas and/or disease conditions.

The method 300 includes delivering 310 electrical stimulation to a target site within the brain at a plurality of different parameter levels. The electrical stimulation can be delivered 310 in a series of pulse groups, as in FIG. 1, where different pulse energy parameters are used between the different pulse groups. In some embodiments, the different parameter levels correspond to different energy levels, such as different pulse amplitudes, widths, frequencies (e.g., the frequency at which pulses within a group are delivered), and/or currents between the groups. In some embodiments, only one pulse parameter is varied between the different pulse groups (e.g., just pulse amplitude) to test the different energy levels, while in some other embodiments multiple pulse parameters are varied between the different pulse groups. In some embodiments, a pulse parameter is incremented or decremented between each pulse group. For example, a scan of different pulse voltages could be performed in increments of one tenth of a volt for each pulse group, the different voltages corresponding to the stimulation parameter spectrum of FIG. 2.

The method 300 also includes sensing 320 a baseline bioelectrical activity level and a bioelectrical response to the stimulation delivery 310 for each of the different levels of the stimulation parameter. Sensing 320 bioelectrical activity can include sensing LFP signals with one or more electrodes in the hippocampus, as discussed herein, or other target location. Sensing 320 to determine the baseline bioelectrical activity level can be done before or after delivery 310, but in any case is done at a time when the target brain area will be unaffected by stimulation so that a baseline bioelectrical activity level can be established based on intrinsic brain activity. As discussed herein, determining the baseline activity level can be used to determine when brain activity is suppressed due to stimulation and when it is unusually high due to stimulation (e.g. corresponding to an after-discharge).

Sensing 320 of a bioelectrical response to the stimulation delivery 320 can be performed during and/or immediately following the delivery 310 of stimulation at a respective stimulation parameter level of the plurality of different levels of the stimulation parameter. Preferably, the respective deliveries of stimulation at the plurality of different levels are separated from each other in time to allow the response of the brain area of each delivery at a particular stimulation parameter level to be fully recognized free of the effects of the stimulation delivery at the other parameter levels. It is noted that while the flowchart of the method 300 has the delivery 310 and sensing 320 steps sequentially, the steps may be performed at the same time and/or interspaced for delivery 310 and sensing 320 for each delivery of stimulation at a different parameter level.

Based on the sensed 320 baseline bioelectrical activity level and the bioelectrical responses for the plurality of different stimulation parameter levels, a suppression window 330 can be identified. The suppression window can be identified 330 as being defined by a suppression threshold as a lower boundary and an after-discharge threshold as an upper bound along a spectrum of the stimulation parameter.

Suppression can be detected as a reduction is bioelectrical activity relative to a baseline level (e.g., as a reduction by 25% or some other amount) during and/or following delivery 310 of electrical stimulation at a particular parameter level. The amount of the reduction used to detect suppression may be a predetermined value or may be selected (e.g., for a particular patient) based on patient condition, disease state, one or more monitored parameters of the patient, and so on. In some cases, the amount may be selected based on a database containing historical patient data, including data for patients having a similar condition, disease state, and so on, as the current patient. In some cases, the value used for this amount may be dynamically adjustable.

An after-discharge can be detected as a surge in bioelectrical activity relative to a baseline level (e.g., as a sudden increase by 25% or some other amount) during and/or immediately following delivery 310 of electrical stimulation at a particular parameter level. As was the case with the value used to detect suppression, the amount used to detect an after-discharge may be a predetermined value or may be selected (e.g., for a particular patient) based on patient condition, disease state, one or more monitored parameters of the patient, and so on. In some cases, the amount may be selected based on a database containing historical patient data, including data for patients having a similar condition, disease state, and so on, as the current patient. In some cases, the value used for this amount may be dynamically adjustable.

Detecting suppression and after-discharge events as well as thresholds and windows can be performed in various manners, such as by using the techniques discussed in connection with FIG. 4 or elsewhere herein.

Parameters for a stimulation therapy can be set 340 based on the suppression window. According to various embodiments, the stimulation parameters are set 340 at a level within the identified 330 suppression window (i.e. at a parameter level above the suppression threshold and below the after-discharge threshold). In some embodiments, the stimulation parameters are set 340 at a level weighted to a lower parameter level (i.e. closer to the suppression threshold than to the after-discharge threshold) within the identified 330 suppression window, such as at ¼ or ⅓ of the span of the window.

Multiple stimulation energy parameters can be tested in various embodiments. For example, the method 300 of FIG. 3 (or any other method herein) can be repeated for each of a plurality of different stimulation parameters. For example, a first scan can test stimulation amplitude as the stimulation parameter, and a second scan can test pulse width, and a third scan can test the pulse frequency. Suppression windows can be identified for each of the different energy parameters. Stimulation therapy parameter levels can then be set 340 for each of the different energy parameters based on respective suppression windows. In some embodiments, a single scan can vary multiple different energy parameters.

In various embodiments, the scan of the method 300 (e.g., the delivery 310, sensing, 320 and identification 330 steps) are performed repeatedly for a plurality of different electrodes (in unipolar stimulation mode) and/or electrode combinations (in bipolar stimulation mode). A preferred electrode or electrode combination can then be selected for therapy delivery and a therapy parameter level within the suppression window of the selected electrode or electrode combination can be set 320. In some embodiments, the preferred electrode or electrode combination for therapy delivery can be selected based on which electrode or electrode combination produced the suppression window with the lowest suppression threshold as a lower boundary (i.e. the lowest stimulation parameter that caused suppression) amongst multiple electrodes and/or electrode combinations scanned (e.g., in the manner of FIG. 3). A lower suppression threshold means that the therapy can be delivered at a lower setting, saving power and minimizing the chances of unintended stimulation, and accordingly an electrode or electrode combination that can be used to deliver therapy at the lowest energy level would be preferred relative to other electrodes and electrode combinations associated with higher suppression thresholds. In some embodiments, the preferred electrode or electrode combination for therapy delivery can be selected based on which electrode or electrode combination produced the widest suppression window (i.e. the greatest parameter range between the suppression threshold and the after-discharge threshold). The widest suppression window allows for the greatest range to vary a stimulation parameter, which may be useful if a user is permitted to adjust the stimulation parameter within the suppression window or a closed-loop therapy control can vary the stimulation parameter within the window.

As shown above, a method can be used to determine a profile of which stimulation parameter(s) cause suppression without after-discharges. The profile can also include which stimulation parameters of different stimulation electrode and/or electrode combinations cause suppression and after-discharges. A scan to determine the suppression and after-discharge thresholds is feasible because, as demonstrated in the data discussed above, the suppression window is bounded by the after-discharge threshold. As such, a scan of stimulation responses from no-suppression to after-discharge can profile a window for managing therapy delivery. In some embodiments, a report can be generated for clinician review showing the suppression and after-discharge thresholds of a suppression window. If an implantable medical device performs the scan, then the profile can be wirelessly transmitted to an external device for display. In some embodiments, the report can resemble the chart of FIG. 2.

It is noted that any and all of the steps and options discussed in connection with FIG. 3, or otherwise discussed herein, can be performed automatically by a medical device. For example, control circuitry of an implantable medical device may perform the steps of the method 300 of FIG. 3 without user intervention to manage therapy delivery.

Figure 4:
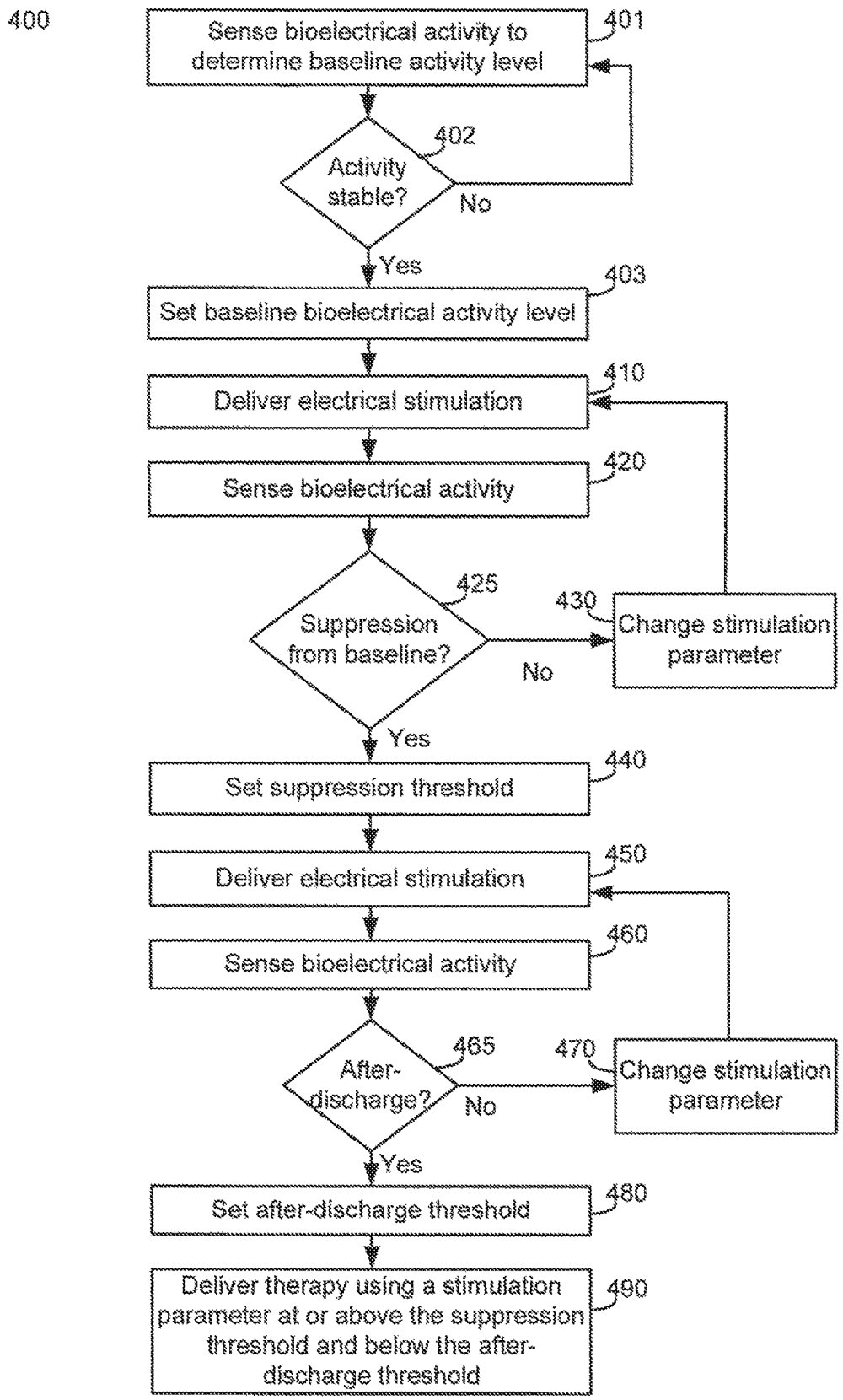
FIG. 4 is a flowchart for identifying thresholds and delivering stimulation.

FIG. 4 shows a flowchart of a method 400 for determining stimulation parameters. The stimulation parameters could be used for the treatment of epilepsy, such as suppressing seizures associated with temporal lobe epilepsy with hippocampal stimulation. However, the techniques of FIG. 4 could be applied to various other brain areas and/or disease conditions.

The method 400 includes sensing 401 bioelectrical activity within a brain at a sense location to determine a baseline bioelectrical activity level. Sensing 401 bioelectrical activity can include sensing LFP signals with one or more electrodes in the hippocampus or other location as a sense location. Sensing 401 can be performed over a predetermined amount of time to get a broad measure of bioelectrical activity of the sense location, such as an amount of time ranging from between 30 seconds and 10 minutes. Examples include fifty seconds or five minutes, although other time periods are contemplated. In various embodiments, no stimulation is delivered during sensing 401 so that a baseline can be determined without the influence of stimulation.

Stability check 402 can be performed to determine whether the sensed 401 bioelectrical activity is stable. In various embodiments, the bioelectrical activity is stable when the RMS or energy (e.g., spectral energy within a particular frequency band) of the LFP signal does not deviate by a threshold amount (e.g., 10% or other predetermine amount from the RMS or energy level) for a predetermined amount of time, among other techniques for assessing bioelectrical activity stabilization of a brain area. Once the bioelectrical activity is stable, then a baseline bioelectrical activity level can be set 403. If variation in the bioelectrical activity prevents setting 403 the baseline, then the method 400 can continue sensing 401 bioelectrical activity and checking 402 whether bioelectrical activity stabilization has occurred until a baseline can be set 403.

Once the baseline is set 403, electrical stimulation can be delivered 410 to a target site within the brain. The target site may be the same brain area as the sense location, such as the hippocampus. However, in various embodiments, the sense location and target site for stimulation are different areas of the brain that are networked. In some embodiments, the target site will correspond to an electrode or electrode combination used for stimulation, such that different target sites are stimulated by different electrodes or electrode combinations. In some examples, multiple sites may be selected for stimulation and/or multiple sites may be selected for sensing. One or more of the multiple sites used for sensing may, but need not, be the same sites used for delivery of the stimulation. Delivery 410 of the electrical stimulation may comprise delivery of a group of pulses as referenced herein, such as a brief series of pulses output using particular energy parameters, e.g., amplitude, current, width, and frequency of pulses within the group.

At the same time as the delivery 410 of electrical stimulation, and/or following the delivery 410 of electrical stimulation, bioelectrical activity is sensed 420 within the brain at the sense location. As discussed herein, electrical stimulation can have a suppressive effect on electrical brain activity, which can be associated with a lower incidence of seizure or other therapeutic benefit. As such, sensing 420 can be performed to determine whether bioelectrical activity has decreased from the baseline in association with delivery 410 of the electrical stimulation.

Suppression check 425 can determine whether the bioelectrical activity level has decreased from the previously set 403 baseline. Brain activity suppression from stimulation can be identified in various ways, as discussed herein. Depending on how the baseline is measured (e.g., RMS, signal energy), a 20% decrease in the measure of brain activity from the baseline during sensing 420 could indicate suppression due to the delivery of electrical stimulation 410. The amount of the decrease used to detect suppression may be selected, in some cases, based on historical patient data gathered from other patients having a same or similar condition and/or disease state. Depending on the predetermined amount of change from baseline (e.g., 20%, 50%, or other amount) for detection, suppression check 425 can be passed if sufficient suppression is identified. If the predetermined amount of change from baseline is not detected during and/or following delivery 410 of electrical stimulation, then the method 400 can change 430 a stimulation parameter and then continue delivering 410 electrical stimulation with the changed parameter.

In various embodiments, changing 430 a stimulation parameter will comprise increasing a stimulation energy parameter in an effort to bring about the suppression. Energy parameters can include pulse amplitude (e.g., current or voltage), width, and frequency, among other parameters. In this way, repeated failure to sense 420 a signal having a characteristic of a suppression effect produced through stimulation delivery 410, as verified by suppression check 425, causes repeated increasing of stimulation energy by changing 430 the stimulation parameter in an incremental manner until a stimulation energy level is reached that suppresses bioelectrical activity in the target area. Although this example concerns an incrementing energy level change, other manners of changing 430 a stimulation parameter could be used, such as a decrementing change in a downward scan.

In some embodiments, suppression check 425 must confirm a sustained suppression to be passed, such as determining whether the suppression of bioelectrical activity persists for a predetermined about of time (during and/or following delivery 410 of electrical stimulation), such as ten seconds, one minute, or some other amount of time.

Upon the recognition of suppression of the bioelectrical activity in the brain area by suppression check 425, a suppression threshold can be set 440. The suppression threshold 440 can be set based on the identification of a stimulation setting that produces a suppression effect of bioelectrical activity after changing 430 a stimulation parameter from a level that failed to pass the suppression check 425. The suppression threshold can be set 440 at the lowest level of a stimulation parameter (e.g., amplitude, pulse width, frequency, or other energy parameter) that produces a suppressive effect in the targeted brain area. For example, if a scan as described above was incrementing pulse voltage by a tenth of a volt for each change 430 in a stimulation parameter, and suppression was recognized by suppression check 425 following the delivery 410 using 1.4 volts but not using 1.3 volts, then 1.4 volts may be selected as the suppression threshold. In some cases the suppression threshold is set 425 at some amount above the lowest stimulation parameter that produced the suppression effect to provide a margin of safety, such as in cases where therapy parameters are later set at or very close to the suppression threshold.

While the steps of delivering stimulation 410, sensing 420, checking 425, and changing 430 can be repeated in a loop to scan a parameter range for a suppression threshold, further steps in the method 400 can continue the scan to identify other notable aspects of a patient's response to different stimulation outputs. The method 400 can continue with the scan with the same output parameters that produced the suppression effect. Delivering 450 electrical stimulation and sensing 460 bioelectrical activity at the same time as stimulation delivery 450 and/or following deliver 450 can be done in the same manner as delivering 410 electrical stimulation and sensing 420 bioelectrical activity, except that the sensed 460 bioelectrical signal(s) are analyzed for evidence of an after-discharge episode for the after-discharge check 465.

It is unlikely that the same parameters that previously produced the suppression effect are also going to cause an after-charge in the scan, per the after-discharge check 465, and in which case the stimulation parameters can be changed 470. The change 470 in stimulation parameters can be an increase in stimulation energy, such as an increment in a stimulation parameter (e.g., pulse or waveform amplitude, width, frequency, or other energy parameter). In some embodiments, the stimulation parameter change 430 and 470 steps implement the same change, such as a pulse amplitude increment of the same amount, while in other embodiments the steps implement different parameter changes.

The loop of the steps of delivering 450 electrical stimulation, sensing 460 bioelectrical activity, monitoring for after-charge at after-discharge check 465, and changing 470 a stimulation parameter can be repeated in a loop until an after-discharge episode is detected, passing after-discharge check 465. An after-discharge threshold can then be set 480 based on the identification of a stimulation setting that produces an after-discharge after changing 470 a stimulation parameter from a level that failed to pass the after-discharge check 425. The after-discharge threshold can be set 480 at the lowest stimulation parameter level that first produced an after-discharge episode. In some cases, the after-discharge threshold can be set 470 at an amount below the lowest stimulation parameter level that first produced the after-discharge effect to provide for a margin of safety, in case a therapy parameter is set to actively use the after-discharge threshold (e.g., as an upper-bound of a closed loop algorithm or as an upper stimulation limit on a user control).

Based on the suppression threshold being set 440 and the after-discharge threshold being set 480, a suppression window can be identified, with the lower bound being the suppression threshold and the upper bound being the after-discharge threshold. The suppression window represents the range of a stimulation parameter that can produce the therapeutic suppression effect without triggering an after-discharge. The suppression window can be used for setting therapy parameters, and in some cases can define a range within which an algorithm or user can actively change a stimulation parameter.

The method 400 further includes delivering 490 stimulation therapy to the patient using a stimulation parameter at or above the suppression threshold and below the after-discharge threshold. In some embodiments, a clinician or circuitry can select a particular parameter level within the suppression window, such as a stimulation parameter level midway between the suppression threshold and the after-discharge threshold, for therapy delivery. In some embodiments, the selected parameter level is weighted to be closer to the suppression threshold than the after-discharge threshold along the parameter spectrum, such as one firth, one quarter, or one third of the way between the suppression threshold than the after-discharge threshold.

It is noted that therapy delivery 490 can comprise pulses delivered at 80 Hz or greater, and 100 Hz or greater, and 80-140 Hz in some embodiments, however not all embodiments are so limited, as pulses can be delivered at higher and lower frequencies.

Multiple stimulation energy parameters can be tested in various embodiments. For example, the method 400 of FIG. 4 (or any other method herein) can be repeated for each of a plurality of different stimulation parameters. For example, a first scan can test stimulation amplitude as the stimulation parameter, and a second scan can test pulse width, and a third scan can test the pulse frequency. Suppression and after-discharge thresholds can be identified for each of the different energy parameters. Therapeutic stimulation can then be delivered 490 to the target location based on the respective suppression and after-discharge thresholds. In some embodiments, a single scan can vary multiple different energy parameters.

In various embodiments, the scan of the method 400 to set the 440 suppression threshold and set 480 the after-discharge threshold are performed repeatedly for a plurality of different electrodes (in unipolar stimulation mode) and/or electrode combinations (in bipolar stimulation mode). A preferred electrode or electrode combination can then be selected, and an energy level above the suppression threshold yet below the after-discharge threshold, can be selected for therapy delivery 490 using the selected electrode or electrode combination. Electrode or electrode combination selection can be done in any manner, such as any manner described herein.

It is noted that any and all of the steps and options discussed in connection with FIG. 4, or otherwise discussed herein, can be performed automatically by a medical device. For example, control circuitry of an implantable medical device may perform the steps of the method 400 of FIG. 4 without user intervention. In some cases, some or all of the steps may be performed by an external device or an external device operating in cooperation with an implantable medical device.

It is noted that the methods 300 and 400 can correspond to the same embodiments, with the flowcharts and discussions of FIGS. 3 and 4 highlighting different aspects of parameter selection. It is also noted that not all embodiments will perform each of the steps of the methods presented herein, and modifications to the methods are contemplated, whether by omitting and/or adding steps. Each of the methods discussed herein can be fully or partially implemented in control circuitry of an implantable medical device (e.g., a neurostimulator configured for DBS) and/or an external device.

Various embodiments of this disclosure identify suppression and after-discharge thresholds. A suppression threshold can be identified in various different ways. Similarly, an after-discharge threshold can be identified in various different ways. For example, a suppression threshold may be identified based on the greatest pulse parameter level that did not cause suppression of the brain area out of a plurality of different pulse parameter levels or the lowest pulse parameter level that did cause suppression of the brain area out of a plurality of different pulse parameter levels. In various embodiments, an after-discharge threshold may be identified based on the greatest pulse parameter level that did not cause an after-discharge event out of a plurality of different pulse parameter levels or the lowest pulse parameter level that did cause an after-discharge event out of a plurality of different pulse parameter levels. It is noted that the identification of a suppression threshold or an after-discharge threshold does not necessarily mean determining the exact parameter level to the finest resolution possible, but rather can include recognizing the relevant stimulation effects on both sides of the threshold from a plurality of different pulse parameter levels while changing the stimulation parameter. For example, a suppression threshold can be isolated by delivering electrical stimulation at a first parameter setting and failing to get a suppression effect, increasing the stimulation energy to a second parameter setting, and recognizing the suppression effect from delivery of electrical stimulation at the second parameter setting. Furthermore, the after-discharge threshold can be isolated by increasing the stimulation energy to a third parameter setting and then further to a fourth parameter setting and recognizing the suppression effect from delivery of electrical stimulation at the third parameter setting and the after-discharge effect from delivery of electrical stimulation at the fourth parameter setting.

In some embodiments, the suppression caused by electrical stimulation will reduce bioelectrical activity across all brain frequencies as in FIG. 1, or substantially all brain frequencies. In some embodiments, the suppression caused by electrical stimulation will reduce bioelectrical activity in a particular frequency band associated with a neurological condition, such as the beta band, which may be therapeutic for various movement disorders. Suppression may be a reduction effect on bioelectrical activity in various embodiments, where the reduction effect does not necessarily decrease all or a substantial amount of brain activity, but rather reduces some aspect of bioelectrical activity associated with a problematic or neurological condition. For example, electrical stimulation can be delivered to reduce particular patterns associated with a neurological condition but not reduce all bioelectrical activity of the targeted area. The reduction effect might be a reduction in the amplitude, energy level, or another measure of intrinsic bioelectrical activity of the targeted brain area.

In various embodiments, control circuitry determines the level of brain activity of a brain area based on at least one characteristic of the bioelectrical brain signal, which can be a time domain characteristic. For example, the level of bioelectrical activity of brain area can be indicated by the average, peak-to-peak, peak, median, lowest amplitude, or instantaneous amplitude of a bioelectrical brain signal sensed within the brain area over a predetermined period of time (e.g., the average amplitude over about one second to about five minutes following the delivery of stimulation to the hippocampus) or the peak-to-peak variability of the bioelectrical signal. As other options, the level of brain activity of a brain area can be indicated by the variance between the instant, median, or mean amplitude of a bioelectrical signal over time, where the variance may be between subsequent slots of time or between a sensed bioelectrical brain signal and a stored average, peak, mean or instantaneous of the amplitude determined based on some predetermined period of time.

In various embodiments, control circuitry may determine the level of bioelectrical activity of a brain area based on a frequency domain characteristic of a bioelectrical signal sensed from the brain area. Examples of a frequency domain characteristic include, but are not limited to, a power level in one or more frequency bands of a bioelectrical signal sensed over a predetermined period of time or a ratio of power levels in at least two frequency bands of the bioelectrical brain signal. The frequency domain characteristic can be determined based on, for example, a spectral analysis of a bioelectrical brain signal. The spectral analysis may indicate the distribution over frequency of the power contained in a signal, based on a finite set of data. In various embodiments, the frequency domain characteristic may comprise a relative power level in a particular frequency band or a plurality of frequency bands. While "power levels" or "energy levels" within a selected frequency band of a sensed bioelectrical brain signal are generally referred to herein, the power or energy level may be a relative power or energy level. A relative power or energy level may include a ratio of a power level in a selected frequency band of a sensed brain signal to the overall power of the sensed brain signal. The power or energy level in the selected frequency band may be determined using any suitable technique. In some examples, control circuitry may average the power or energy level of the selected frequency band of a sensed brain signal over a predetermined time period, such as about ten seconds to about two minutes, although other time ranges are also contemplated. In other examples, the selected frequency band power or energy level may be a median level over a predetermined range of time, such as about ten seconds to about two minutes. The activity within the selected frequency band of a bioelectrical signal sensed from a brain area, as well as other frequency bands of interest, may fluctuate over time. Thus, the power or energy level in the selected frequency band at one instant in time may not provide an accurate and precise indication of the energy of the bioelectrical signal in the selected frequency band. Averaging or otherwise monitoring the power or energy level in the selected frequency band over time may help capture a range of levels, and, therefore, a better indication of the state of the brain area.

The overall power or energy of a sensed bioelectrical brain signal may be determined using any suitable technique. Control circuitry may determine an overall power or energy level of a sensed bioelectrical brain signal based on the total level of a swept spectrum of the bioelectrical signal. To generate the swept spectrum, a processor may control a sensing module to tune to consecutive frequency bands over time, and the processor may assemble a pseudo-spectrogram of the sensed bioelectrical signal based on the power or energy level in each of the extracted frequency bands. The pseudo-spectrogram may be indicative of the energy of the frequency content of the bioelectrical signal within a particular window of time.

In some cases, the baseline brain activity level may represent an intrinsic patient condition that is undesirable (e.g., a brain state in which one or more symptoms associated with the patient disorder to be treated via therapy are observed or a brain state in which an unwanted event is likely to occur). Control circuitry may identify one or more characteristics of a sensed bioelectrical brain signal and store the identified characteristic(s) as indicators of the baseline brain activity level. For example, the baseline brain activity level of a brain area can be indicated by the average, peak-to-peak, peak, mean or instantaneous amplitude of a bioelectrical signal sensed from the brain area (e.g., the hippocampus) over a predetermined period of time (e.g., the average amplitude over a period of time of about five seconds to about five minutes), the variability of the bioelectrical brain signal over time, a frequency domain characteristic (e.g., a relative power or energy in a particular frequency band or a ratio of power or energy levels), or a variability of one or more frequency domain characteristics (e.g., the average, peak, mean or instantaneous energy level within a selected frequency band over predetermined period of time) over time, among other options. A change in the level of bioelectrical activity from the baseline in a brain area associated with the delivery of stimulation to the area (or a different but functionally connected brain area) characterizing a suppression effect can be a percentage change of the bioelectrical activity level relative to the baseline bioelectrical activity level, a gross value indicative of the change in the bioelectrical activity level relative to the baseline brain activity level, or any combination thereof. For example, if the level of brain activity in the hippocampus is indicated by an amplitude of a bioelectrical brain signal, the change in the level of brain activity in the hippocampus resulting from the delivery of stimulation to the same or different area of the brain characterizing the suppression effect can be a predetermined difference associated with a clinical therapeutic benefit between the baseline amplitude and the amplitude of the bioelectrical signal sensed within the hippocampus over a predetermined duration of time during and/or following the delivery of stimulation. Other parameters besides amplitude are also contemplated for measuring a change from a baseline level of bioelectrical activity of a brain area to characterize suppression or after-discharge. In various embodiments, the change in the signal relative to a baseline must be greater than a threshold amount for control circuitry to confirm a particular event or brain state, such as an after-discharge or suppression.

The techniques disclosed herein can employ a supervised machine learning algorithm (e.g., utilizing a support vector machine or another artificial neural network) to develop one or more discriminators for detecting different brain states. The different states can correspond to states of no suppression, suppression, and after-discharge, such as in FIG. 2. The detection of the different brain states can be automated based on the discriminators, such as for automatic detection by control circuitry.

In implementing such a supervised machine learning technique, control circuitry can receive a bioelectrical signal (e.g., a LFP signal sensed from the hippocampus) that represents multiple episodes of different patient states and extract characteristics from the signal. A clinician can review the extracted information and/or observe the patient to determine at which times the patient had a first, second, or third brain state. For example, a clinician can look at the data of FIG. 1 to identify particular patient states (e.g., baseline, no suppression, suppression, and after-discharge) and annotate them accordingly. These clinician assessed brain state determinations can be temporally associated with the extracted signal characteristics. The extracted characteristics and brain state information can be used to generate a classification boundary delineating a first brain state (e.g., suppression) and a second brain state (e.g., no suppression). A classification boundary can also be set delineating additional patient states, such as suppression and after-discharge brain states. Examples of signal characteristics that can be extracted from a sensed signal include a morphology of the signal (e.g., amplitude, slope, frequency, peak value, trough value, or other traits of the signal), the spectral characteristics of the signal (e.g., frequency band power level, a ratio of power levels, and the like), and/or any other signal characteristics referenced herein.

The boundary can be formed in feature space using a supervised machine learning algorithm. Feature space plots instances of samples in patterns in n-dimensional space, the dimensions being determined by the number of features used to describe the pattern. A feature is a characteristic of a signal parameter (e.g., indicating suppression or after-discharge). Each feature of feature space defines an axis, such that the values of a feature vector (e.g., parameter data plotted in feature space for one brain state instance) indicate the coordinates of a point within the feature space. A feature vector is a vector defined by two or more feature values indicative of respective parameters. A feature vector can be mapped to a point within feature space based on the values of the features in the feature vector. Each feature vector defines a point in feature space that a support vector machine implemented by a computing device can use to classify data. Each data point feature vector is a quantitative representation of the monitored feature values for a given time slice (e.g., a short window of time) and each feature vector defines a data point in the feature space that can be used, together with other feature vectors as data points, to generate a boundary or establish some other relationship (e.g., to be used to discriminate between baseline, no suppression, suppression, and after-discharge states).

Training data can initially be used during a training phase to populate feature space and determine a boundary based on known occurrences of the different patient states. The occurrences of the different patient states may be known because, as described above, they are evaluated by a clinician. For example, a clinician can review data of multiple episodes (e.g., representing samplings of baseline, no suppression, suppression, and after-discharge patient states) similar to that of FIG. 1. A brain state indication may then be associated with corresponding data segments or signal characteristic levels (e.g., RMS, spectral energy) and input into a computing device.

A boundary can be set within feature space delineating the feature vectors of the different patient states. Such a process can then train the algorithm by setting the linear discriminate to differentiate different patient states based on subsequently sensed data. Parameter information can be extracted from the later sensed signal and compared to the boundary to determine whether the patient is in the first brain state (e.g., similar to baseline with no suppression), the second brain state (e.g., suppressed brain activity), or a third brain state (e.g., an after-discharge episode) based on which side of the boundary or boundaries the subsequent data (e.g., in the form of a feature vector) would lie in feature space.

Training data feature values can be based on data from one particular patient to be used in classifying future brain states for the particular patient or for classifying future brain states of a different patient. In some cases, feature values are based on more than one patient and could be used in classifying future brain states for one or more patients. For instance, the feature values may be developed based on data stored in a database for patients that may have similar conditions and disease states as the current patient.

Figure 5:
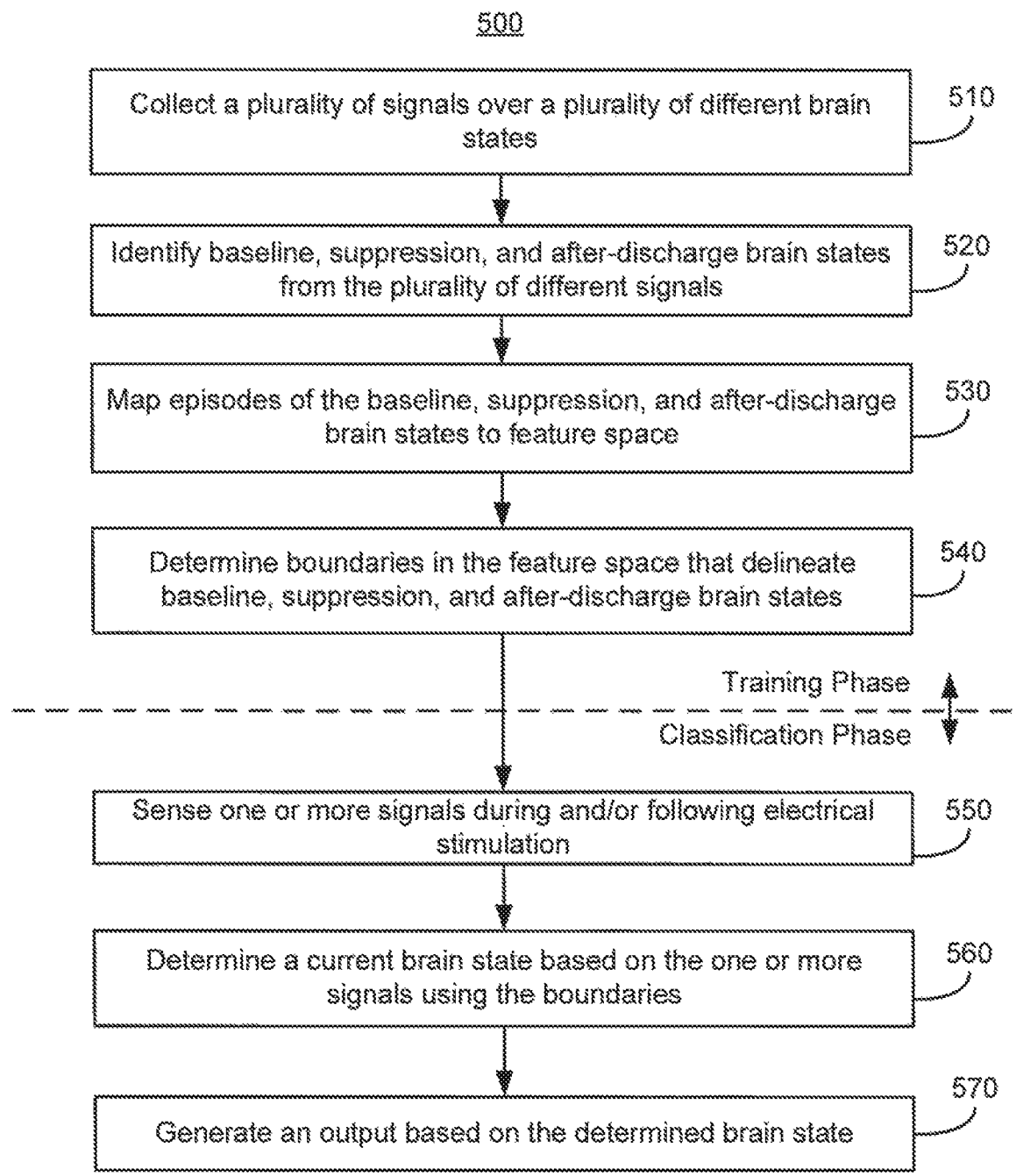
FIG. 5 is a flowchart for detecting patient states.

FIG. 5 illustrates a flow chart for a method 500 for determining a boundary that can be used in classification of a brain state and then monitoring the brain state of a patient. The method 500 includes collecting 510 a plurality of signals over a plurality of different brain states. The brain states can be baseline (no suppression), suppression, and after-discharge states, however additional or alternative brain states could be used. Collecting 510 in this manner may be done in the same manner of the delivering 310 and sensing 320 steps of FIG. 3, and/or in any other manner referenced herein. Collecting 510 can include sensing signals and storing the signals in memory.

The method 500 further includes identify 520 baseline, suppression, and after-discharge brain states from the plurality of different signals. The baseline, suppression, and after-discharge episodes may be identified based on a characteristic of a LFP signal and/or spectrogram, such as in the manner discussed in connection with FIG. 1. The episodes may be manually noted by a clinician viewing the data and making input in a computing device or the identification of the episodes may be partially or fully automated by control circuitry. A baseline state may be identified based on a LFP signal and/or spectrogram not changing in the absence of stimulation for a predetermined amount of time. A no suppression state may be identified based on a LFP signal and/or spectrogram not changing from baseline (or changing only an insignificant amount) during and/or following stimulation. A suppression state may be identified based on a LFP signal and/or spectrogram showing reduced bioelectrical activity relative to a baseline (e.g., reduced below baseline by a predetermined amount) during and/or following stimulation. An after-discharge state may be identified based on a LFP signal and/or spectrogram showing surging bioelectrical activity following stimulation. For each of the episode identifications 520, the bioelectrical parameter levels sensed at that time can be noted.

Based on these bioelectrical parameter levels associated with the different identified 520 brain states, control circuitry can map 530 episodes of the brain states to feature space. Mapping 530 in this way can generate a feature space plot of episodic feature vectors, with one or more parameters being used for axes in feature space. One or more boundaries may be determined 540 in the feature space using control circuitry, the boundaries delineating the baseline (no suppression), suppression, and after-discharge brain states. For example, a baseline (no suppression) brain state may be on one side of a boundary while a suppression brain state may be on the other side of the boundary, the control circuitry setting the boundary in the separation space between different groupings of feature vectors of common brain states. A boundary may be set manually by a clinician by recognizing groupings of feature vectors of common brain states and setting a boundary within the separation between the different groupings.

Collecting 510, identify 520, mapping 530, and determining 540 comprise an initial training phase. Once the one or more boundaries are determined 540, the boundaries may be used in a classification phase that can classify subsequent patient brain states based on incoming information (e.g., brain state discrimination in real-time). The classification phase can include sensing 550 one or more signals during and/or following stimulation delivery. Characteristics of the signals may be extracted from the sensed 550 signals in the same manner as the identifying 520 brain states step, although the use of different analysis circuitry and/or techniques for the different phases is contemplated. In any case, a current brain state of a patient may be determined 560 based on one or more boundaries and the one or more signals, the boundary serving as a brain state threshold. The current patient state may be determined 560 by control circuitry running a linear discriminant algorithm which can determine on which side(s) of the one or more boundaries a current feature vector is, the current feature vector derived from the one or more sensed 550 signals.

An output may be generated 570 based on the determined 560 brain state. The output may be any output referenced herein, including stopping stimulation (e.g., in the case of an after-discharge), increasing stimulation intensity (e.g., in the case of no suppression), decreasing stimulation intensity (e.g., in the case of an after-discharge), maintaining stimulation energy (e.g., in the case of confirmation of suppression), alerting a patient and/or clinician to the brain state, and/or storing data characterizing the brain state episode of the patient.

In various embodiments, the training phase can be used without the classification phase and the classification phase can be used without the training phase. For example, a boundary may be set using a technique that is substantively different from the training phase of the method 500 and that boundary may be used to classify brain state episodes. Also, the training phase may determine 540 a boundary that is used in a substantively different way as the classification phase of the method 500 to classify patient state episode or for some other purpose. It is noted that the training phase may be performed in accordance to any of techniques discussed in connection with FIGS. 1-4 while the classification phase may be performed in accordance to any of techniques discussed in connection with FIGS. 6-8.

Aspects of detecting various patient states and using feature space, among other things, that can be applied to the present subject matter are disclosed in commonly assigned U.S. Pat. App. No. 2010/0280335 to Carlson et al., which is entitled "PATIENT STATE DETECTION BASED ON SUPERVISED MACHINE LEARNING BASED ALGORITHM" filed Nov. 4, 2010; and U.S. Pat. App. No. 2010/0280334 to Carlson et al., which is entitled "PATIENT STATE DETECTION BASED ON SUPPORT VECTOR MACHINE BASED ALGORITHM" filed Nov. 4, 2010, which are incorporated herein by reference in their entireties.

In some embodiments, a patient or other user is allowed some control over therapy delivery by controlling the input. For example, a patient or other user may increase or decrease therapy intensity as desired by controlling the input (e.g., a switch, button, dial, or other control), but the system will not allow the stimulation parameters to be adjusted (e.g., without specific clinician intervention to override the limitation) to a level outside of the suppression window. In some embodiments, a patient or other user is allowed to adjust stimulation intensity but is not allowed to increase stimulation intensity in a manner that would increase a stimulation parameter above the after-discharge threshold. In some embodiments, a closed loop algorithm is set to automatically change a stimulation parameter of a therapy based on an input. For example, the stimulation parameter may be able to range within the suppression window based on the input in some embodiments but is prevented from deviating outside of the suppression window. In some embodiments, the input is based on a sensed signal, such as a physiological signal, a neurological signal, a cardiac signal (e.g., indicative of heart rate or blood pressure), a posture signal indicative of the posture of the patient, an activity signal indicative of the activity of the patient (e.g. an accelerometer signal indicative of patient movement), or some other signal. The suppression window or threshold used to limit user or automatic therapy adjustment based on an input may be set using any technique herein, such as any of FIGS. 3-5 for example.

Figure 6:
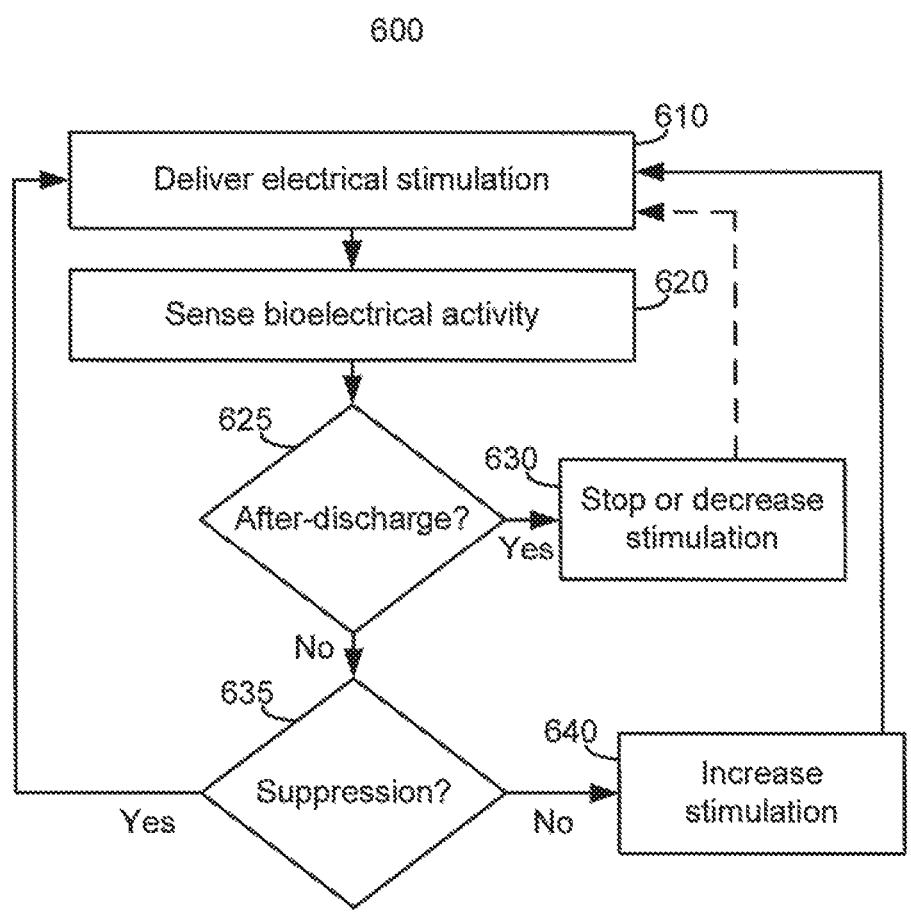
FIG. 6 is a flowchart for managing therapy delivery.

FIG. 6 is a flowchart of a method 600 for controlling a therapy based on detection of suppression and after-discharges. The method 600 can concern embodiments operating according to a closed loop algorithm for controlling a chronic therapy. The therapy may comprise the delivery of a continuous therapeutic signal or train of pulses, monitoring of the bioelectrical response to the stimulation, and changing a stimulation parameter of the stimulation in real-time based on various bioelectrical responses. It is noted that the method 600 can be applied to cycled therapy embodiments where stimulation is cycled on and off according to a duty cycle. Cycled therapy embodiments will be specifically discussed in greater detail in connection with FIGS. 7 and 8.

The method 600 includes delivering 610 electrical stimulation to a brain area, which can be a hippocampus or other brain area. The electrical stimulation can be delivered 610 in any manner referenced herein. The method 600 includes sensing 610 bioelectrical activity of a brain area (e.g., hippocampus), which can be done in any manner referenced herein, and can further be done simultaneously with and/or following delivery 610 of the electrical stimulation.

Based on the sensed 610 bioelectrical activity, after-discharge check 625 and suppression check 635 can be performed. In this way, one or more algorithms can be run using a monitored bioelectrical signal to detect suppression and after-discharge events. Such checks may be performed periodically (e.g., every one minute or other interval), constantly, or performed in response to an event (e.g., an accelerometer or other sensor indicating the occurrence of a seizure or other event). The suppression detection can be performed by any technique referenced herein. In some embodiments, the suppression detection can be performed by comparing a current signal parameter level (e.g., RMS, spectral energy, or other parameter) to a baseline (e.g., a baseline previously set for the patient as discussed herein), where suppression is confirmed as long as the signal parameter is, one example, some predetermined amount or percentage below the baseline, as may be required for some predetermined period of time (e.g., 30% below the baseline level for ten seconds). In some other examples, the check 635 may instead compare the monitored bioelectrical signal to a predetermined fixed level rather than a relative level that is relative to a baseline.

The after-discharge check 625 can be performed by any technique referenced herein for detecting an after-discharge event. In some embodiments, the after-discharge detection can be performed by comparing a current bioelectrical signal parameter level to baseline, where an after-discharge is detected if the signal parameter is a predetermined amount or percentage greater than the baseline for a predetermined period of time (e.g., 30% above the baseline LFP level for ten seconds).

If an after-discharge event is detected by after-discharge check 625, then stimulation is stopped (if it is being delivered). In some cases, the triggering of an after-discharge will suspend therapy delivery and a notification will be issued by an external programmer warning of the condition. The indication of the after-discharge may have to be communicated from an implantable device to an external device if the implanted device performs the after-discharge detection. In some embodiments, stimulation delivery 610 will only be resumed if a clinician provides an input re-enabling therapy. In some other embodiments, stimulation will be resumed at a decreased stimulation energy level following detection of an after-discharge, such as by decrementing a stimulation energy parameter, such as pulse amplitude, width, frequency, or other energy parameter. In some cases, the stimulation delivery 610 will only resume after the after-discharge event is confirmed to have subsided. If an after-discharge event is not detected, then stimulation delivery 610 can continue (or resumed at the next cycle if after-discharge check 625 is performed at the end of a delivery 610 cycle).

A suppression check 635 can also be performed. If suppression is confirmed by suppression check 635, then delivery 610 of the electrical stimulation can continue (or resume at the next cycle if suppression check 635 is performed at the end of a delivery 610 cycle). If suppression is lost as confirmed by check 635, then the method 600 can increase a stimulation energy parameter, such as by incrementing a stimulation output parameter, such as pulse amplitude, width, frequency, or other energy parameter. The step of increasing 630 the stimulation may be performed incrementally, such that each repeated failure to detect suppression at suppression check 635 causes another incremental increase 630 in a stimulation parameter in a looping fashion. In this way, if suppression is lost, then it can be regained by scanning a parameter range (typically with an increasing stimulation energy level) until suppression is regained as confirmed by suppression check 635 or an after-discharge is provoked as confirmed by after-discharge check 625 (in which can an alert message may be output that a suitable stimulation parameters level cannot be resolved).

While the after-discharge check 625 and the suppression check 635 are illustrated as different stages, they could be part of the same detection algorithm or they may otherwise be performed simultaneously. In some embodiments, a suppression window may already be established (e.g., by the techniques of FIGS. 3-5) and the algorithm of FIG. 6 can change the stimulation parameter within the suppression window by decreasing 630 and increasing 640 a stimulation energy parameter as necessary, but the stimulation parameter will not be changed out of the originally set suppression window. In some other embodiments, the algorithm of FIG. 6, or a similar algorithm based on real-time detection of suppression and after-discharge, can be used to automatically titrate one or more stimulation parameters without regard to a previously set suppression window. In some embodiments, the method 600 of FIG. 6, or other method of this disclosure, can be combined with a closed loop or user control algorithm, that can also change the stimulation parameter based on an input as discussed herein. The input may be a user input controlling the therapy level or a sensed signal, as discussed herein. The stimulation parameter level may then change according to the input but detection of an after-discharge (e.g., by after-discharge check 625) can over-ride the input to stop therapy or decrease 630 the stimulation parameter level. Likewise, the stimulation parameter level could change according to the input but detection of loss of suppression (e.g., by suppression check 635) can over-ride the input to increase 640 the stimulation parameter level. Such options are also application to the other embodiments of this disclosure.

As such, the method 600 demonstrates various options for closed loop stimulation of a brain area, such as a hippocampus. Each of the steps of the method 600 and the various options discussed herein can be automatically performed by control circuitry of an implantable medical device to titrate therapy delivery to therapeutically suppress bioelectrical activity while avoiding after-discharges. Actively adapting stimulation parameters can be useful in some cases because the suppression threshold and after-discharge threshold may change over time, which accordingly changes the suppression window. Various factors could potentially cause a threshold to change. Such factors can include changes in the activation thresholds of the neurons, lead migration, changes in the properties of tissues around the lead (e.g., fibrous electrode encapsulation), changes in brain states of the patient (e.g., awake verses asleep states), changes in posture, disease progression, changes in a drug regimen the patient may be taking, and changes in hydration and other factors that can affect brain chemistry, among other reasons that can alter previously established thresholds. Other embodiments are contemplated for adapting stimulation in a closed-loop manner.

It is noted that any and all of the steps and options discussed in connection with FIG. 6, or otherwise discussed herein, can be performed automatically by a medical device (unless specific user steps are specified such as a user input therapy control). For example, control circuitry of an implantable medical device may perform the steps of the method 600 of FIG. 6.

Various embodiments of this disclosure concern the delivery of a cycled therapy, where stimulation is cyclically turned on and off, such as alternating periods of one minute of stimulation delivery (stimulation on) and one minute of no stimulation (stimulation off). In some cases, the benefits of therapy persist during the therapy-off periods in a carry-over effect, which is referred to a washout period. For example, a cycle of stimulation delivery may suppress hippocampal LFP activity and the suppression may persist for a minute or more during a washout period, while the suppression effect eventually subsides and the bioelectrical activity returns to the baseline. Some cycled therapy embodiments resume stimulation following the expiration of a timer, while some other embodiments monitor the level of suppression during the washout period and resume therapy delivery when the suppression effect subsides. Various options for cycled therapy are demonstrated in FIGS. 7 and 8.

Figure 7:
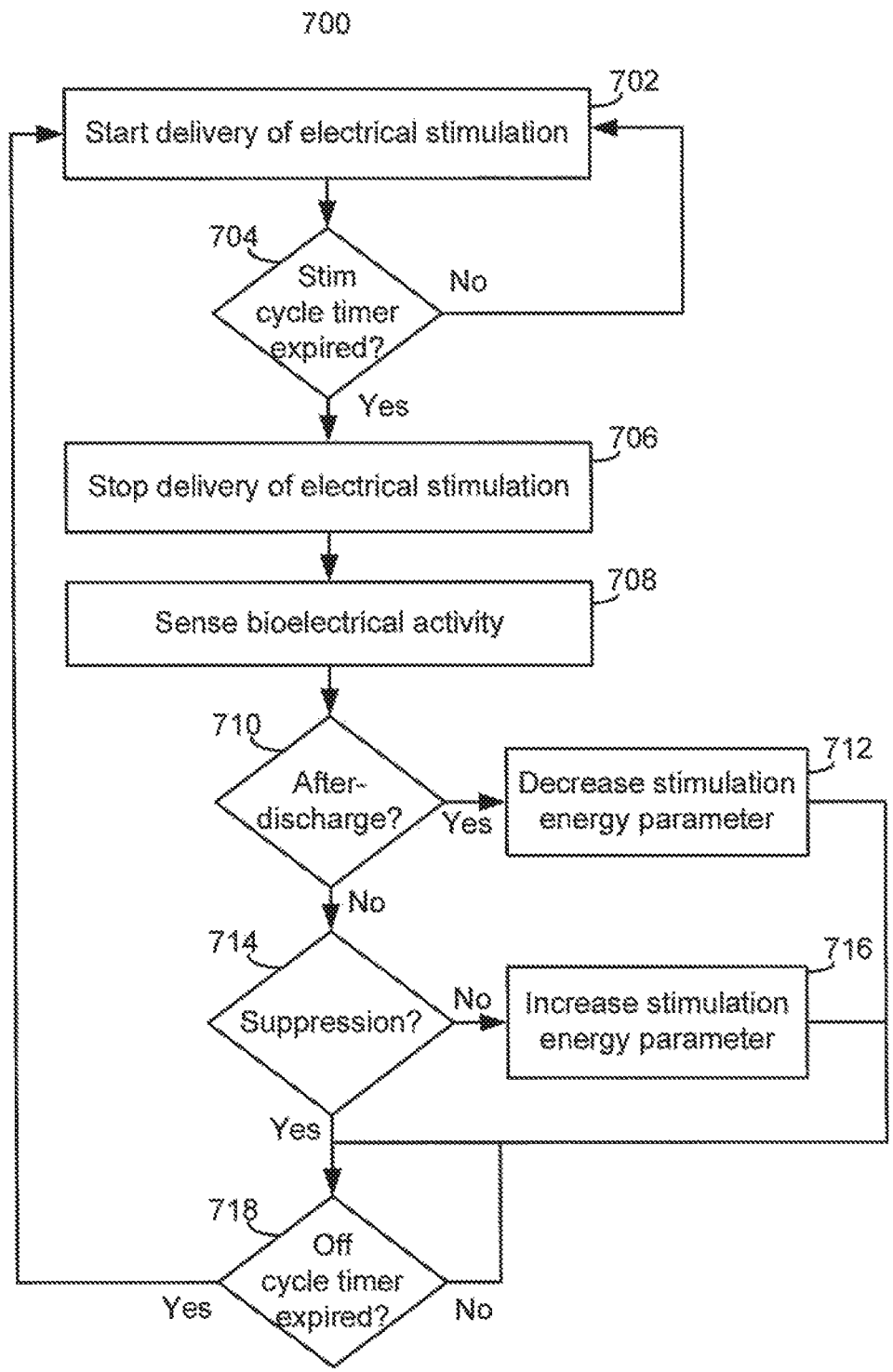
FIG. 7 is a flowchart for managing delivery of a cycled therapy.

FIG. 7 illustrates a flowchart of a method 700 for controlling therapy delivery of a cycled therapy. The method 700 includes starting 702 delivery of electrical stimulation, which can be performed in any manner referenced herein. When the delivery of electrical stimulation is started 702, a stim cycle timer can be started. The stim cycle timer can time how long stimulation is being delivered for each cycle. For example, stimulation may be delivered for a first time period, and then not delivered for a second time period, and the cycle may continuously repeat the first and second cycles. The first time period of cycled stimulation may be one minute, ten minutes, one hour, or other period of time. The second time period of cycled stimulation off may be one minute, ten minutes, one hour, or other period of time. In various embodiments, the first time period of stimulation is equal to the second time period of no stimulation, while in some other embodiments the time periods are not equal.

Check 704 monitors the stim cycle timer and when the stim cycle timer expires the delivery of stimulation is stopped 706. Following the stopping 706 of stimulation, a bioelectrical activity is sensed 708. Sensing 708 of bioelectrical activity may be done in any manner referenced herein, such as sensing 708 of a LFP signal from a hippocampus. Based on the sensed 708 signal, a check 710 is performed for the presence of an after-discharge. Detection of the after-discharge can be done in any manner referenced herein. It is noted that the flowchart of FIG. 7 shows the sensing 708 and after-discharge check 710 being performed after stimulation is stopped 706, however in various embodiments sensing 708 and after-discharge check 710 are performed during stimulation.

If an after-discharge is detected by after-discharge check 710, then a stimulation energy parameter can be decreased 712. The stimulation energy parameter may be decreased 712 by a small amount in a scanning manner, or the stimulation energy parameter may be decreased 712 by a large amount (e.g., by a whole volt or to just above a previously identified suppression threshold) reflecting the desire to avoid subsequent after-discharge events. The method 700 then waits until the off cycle timer check 718 shows that the off cycle time has expired before starting 702 delivery of the electrical stimulation with the decreased 712 stimulation energy parameter for another cycle.

A suppression check 714 can be performed using the sensed 708 bioelectrical activity signals. Suppression may be confirmed using any technique referenced herein. If suppression is identified, then the method 700 waits until the off cycle timer check 718 shows that the off cycle time has expired before starting 702 delivery of the electrical stimulation with the same electrical stimulation parameters used in the previous cycle. However, if suppression is not detected by suppression check 714, then a stimulation energy parameter can be increased 716. Increasing 716 a stimulation energy parameter can be done incrementally (e.g., in 0.1 volt increments) to scan along a parameter spectrum toward a suppression threshold, as discussed herein. The method 700 then waits until the off cycle timer check 718 shows that the off cycle time has expired before starting 702 delivery of the electrical stimulation with the increased 716 stimulation energy parameter for another cycle.

It is noted that any and all of the steps and options discussed in connection with FIG. 7, or otherwise discussed herein, can be performed automatically by a medical device. For example, control circuitry of an implantable medical device may be configured to perform the steps of the method 700 of FIG. 7.

As shown in FIG. 7, some cycled stimulation embodiments turn the delivery of stimulation on and off according to a timing schedule. However, some other cycled stimulation embodiments adjust the timing of the cycle according to a washout period. For example, the suppression level may be monitored during the washout period following a stimulation delivery cycle to determine when the suppression effect subsides to some level, triggering the next cycle of stimulation. Only once the suppression effect decreases and the bioelectrical brain activity increases above a certain amount (e.g., a minimum suppression level representing the lowest acceptable amount of LFP activity or a return to baseline or just below baseline), will the next delivery cycle be started. Some aspects of cycled stimulation based on a washout period are further demonstrated in FIG. 8.

Figure 8A:
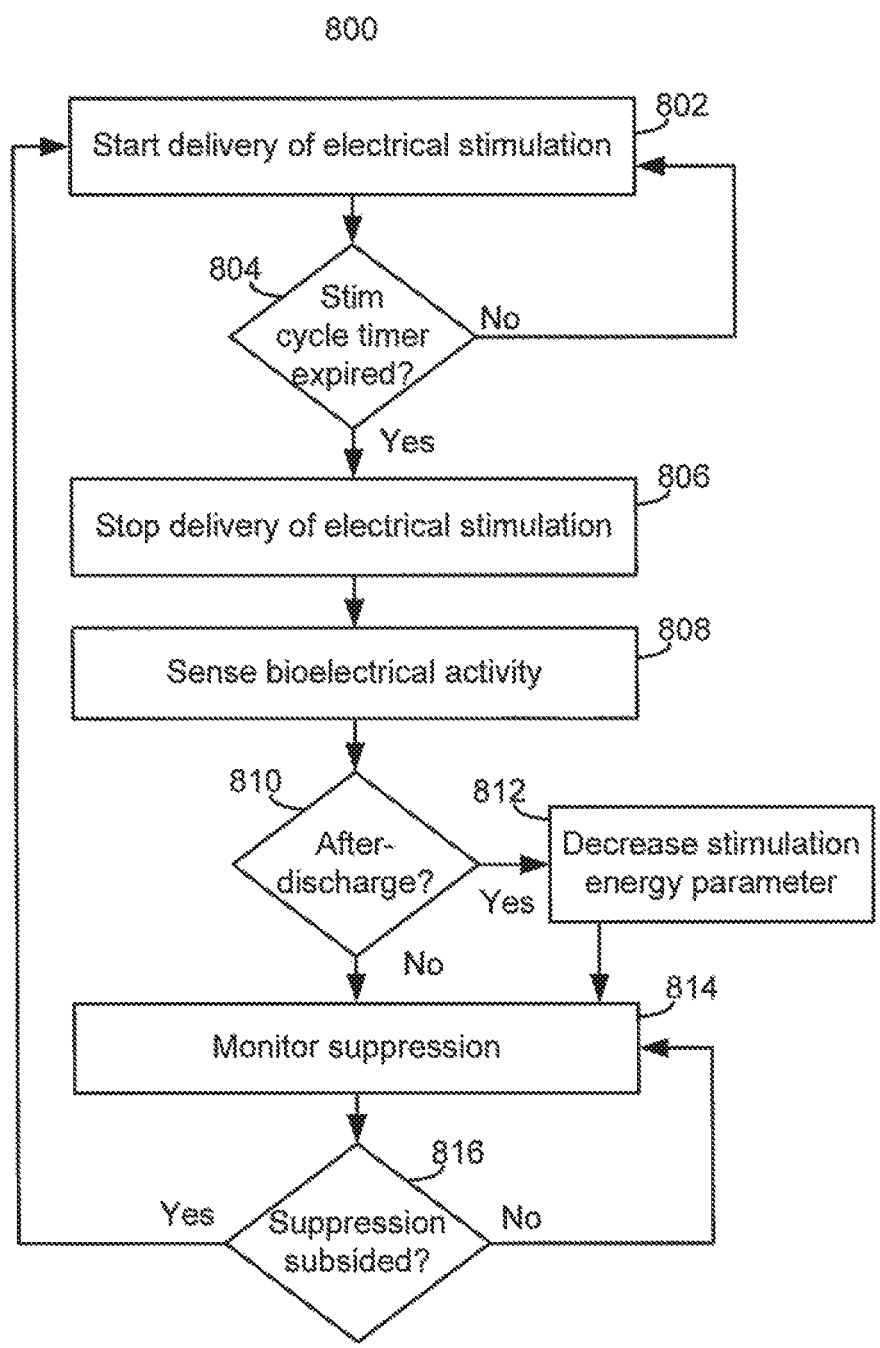
FIG. 8A is a flowchart for managing delivery of a cycled therapy according to a washout period.

FIG. 8A illustrates a flowchart of a method 800 for controlling therapy delivery of a cycled therapy. The method 800 includes starting 802 delivery of electrical stimulation, which can be performed in any manner referenced herein. When the delivery of electrical stimulation is started 802, a stim cycle timer can be started. The stim cycle timer can operate any in manner for controlling the time of delivery of a stimulation cycle, including as described above. Check 804 monitors the stim cycle timer and when the stim cycle timer expires the delivery of stimulation is stopped 806. Following the stopping 806 of stimulation, bioelectrical activity is sensed 808. Sensing 808 of bioelectrical activity may be done in any manner referenced herein, such as sensing 808 of a LFP signal from a hippocampus. Based on the sensed 808 bioelectrical, an after-discharge check 810 is performed for detecting after-discharge. Detection of after-discharge can be done in any manner. It is noted that the flowchart of FIG. 8A shows the sensing 808 and after-discharge check 810 being performed after stimulation is stopped 806, however in various embodiments sensing 808 and after-discharge check 810 are also performed during stimulation.

If an after-discharge event is detected by after-discharge check 810, then a stimulation energy parameter can be decreased 812. The stimulation energy parameter may be decreased 812 in any manner, including as described in connection with other embodiments herein (e.g., FIGS. 6 and 7). The method 800 also includes monitoring 814 for suppression of bioelectrical activity based on the sensed 808 bioelectrical activity. Monitoring 814 for suppression of bioelectrical activity can be done in any manner, including comparing a current level of bioelectrical activity to a minimum threshold or baseline amount. For example, a parameter of a sensed 808 LFP signal and/or spectrogram may be compared to a minimum threshold representing the least amount of suppression deemed suitable before the stimulation cycle is resumed. When the parameter of the sensed 808 LFP signal and/or spectrogram rises above the minimum threshold, as is expected to end the washout period, then the suppression check 816 can determine that the suppression has subsided and the delivery of electrical stimulation can be started 802 for another stimulation cycle. In some embodiments, the monitoring 814 step compares the parameter of the sensed 808 LFP signal and/or spectrogram to a baseline bioelectrical activity level (associated with no stimulation as discussed herein), and when the parameter rises to the baseline level or otherwise evidence that the brain state shows no remaining effect of the stimulation, then the suppression check 816 can be satisfied and the delivery of electrical stimulation can be started 802 for another stimulation cycle. In some cases, the suppression check 816 is satisfied when the monitored 814 parameter level is within a predetermined amount of the baseline, such as 20% of the baseline, which triggers the start 802 of electrical stimulation delivery for another stimulation cycle. In these any other ways, various embodiments herein can monitor the effects of the stimulation and turn on stimulation only when necessary to manage a patient condition.

It is noted that an additional check may be performed that is similar to the suppression check 714 and stimulation energy increase 716 of FIG. 7, where if suppression is not detected following the end of the stimulation cycle, then a stimulation energy parameter can be increased.

It is noted that any and all of the steps and options discussed in connection with FIG. 8A, or otherwise discussed herein, can be performed automatically by a medical device. For example, control circuitry of an implantable medical device may be configured to perform the steps of the method 800 of FIG. 8A.

Figure 8B:
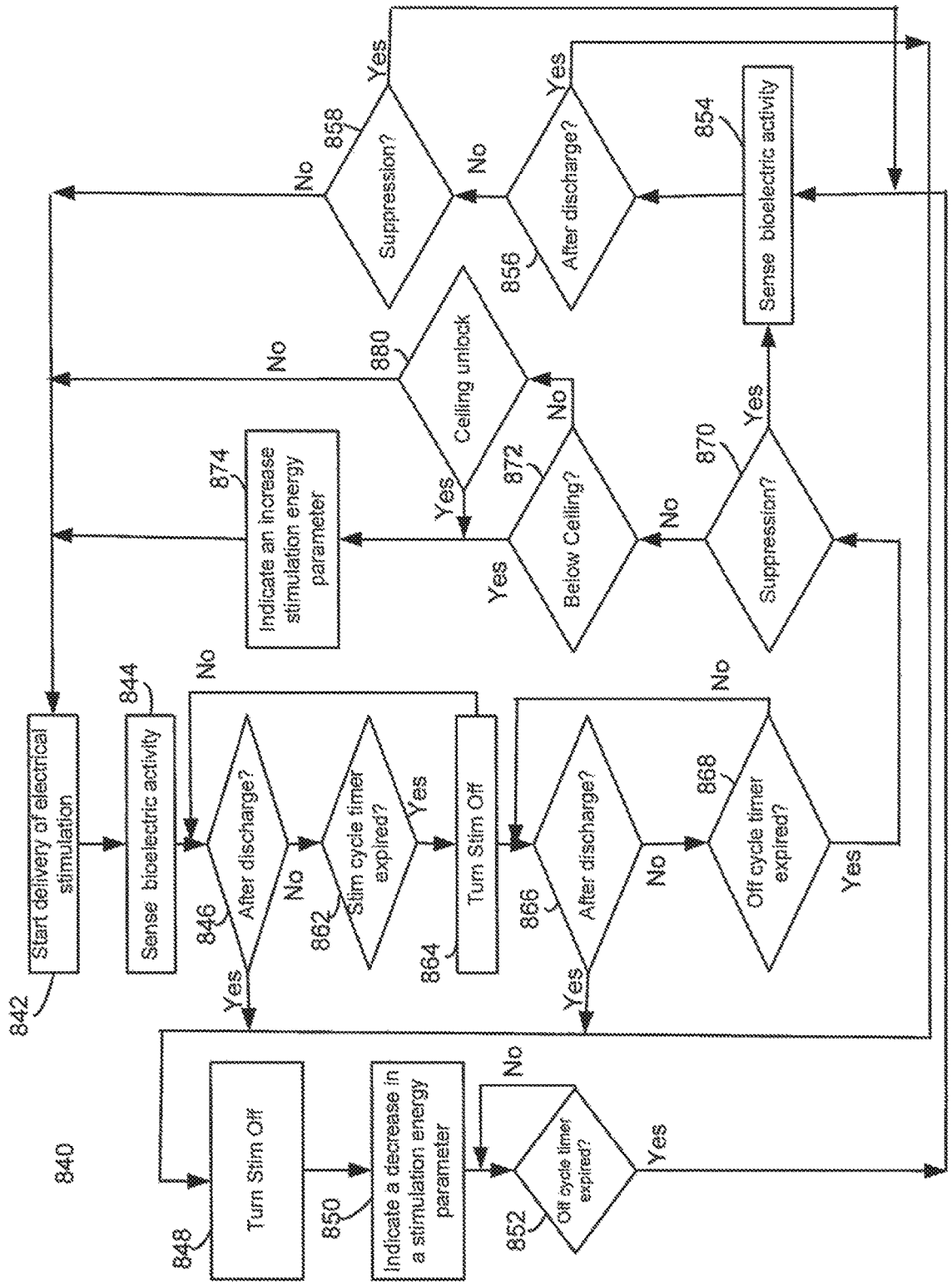
FIG. 8B is another flowchart for managing delivery of a cycled therapy according to a washout period.

FIG. 8B illustrates a flowchart of a method 840 for controlling therapy delivery of a cycled therapy. The method 840 includes starting 842 delivery of electrical stimulation, which can be performed in any manner referenced herein. When the delivery of electrical stimulation is started 842, a stim cycle timer can be started. The stim cycle timer can operate any in manner for controlling the time of delivery of a stimulation cycle, including as described above. Also at this time, a stimulation ceiling level may be initiated, which indicates an upper allowable level that may be used for a stimulation energy parameter, as will be discussed further below.

Following the starting 842 of stimulation, bioelectrical activity is sensed 844. Sensing 844 of bioelectrical activity may be accomplished in any manner referenced herein, such as sensing 844 of a LFP signal from a hippocampus. Based on the sensed 844 bioelectrical signal, an after-discharge check 846 is performed for detecting after-discharge. Detection of after-discharge can be done in any manner referenced herein.

If an after-discharge event is detected by after-discharge check 846, stimulation energy may be turned off 848. Also at this time, an off-cycle timer may be started to control the time stimulation is turned off. In addition, an indication is recorded 850 that indicates that when stimulation is once again turned on, stimulation energy is to be decreased as a result of detecting the after-discharge event. Such an indication may be a flag that indicates stimulation is to be decreased by a predetermined amount or by an amount that may be dynamically-selectable based on patient condition. In another example, such an indication may be a stored value for a stimulation energy parameter that will be used to control stimulation when stimulation is again resumed. Other examples of indicating a decrease 850 in a stimulation energy parameter are provided herein, including as described in connection with, for instance, FIGS. 6 and 7.

Processing then continues to check 852, which monitors for expiration of the off-cycle timer. When this timer expires, bioelectrical activity is sensed 854. Sensing 854 of bioelectrical activity may be done in any manner referenced herein, such as sensing 854 of a LFP signal from a hippocampus. Based on the sensed 854 bioelectrical signal, an after-discharge check 856 is performed for detecting after-discharge. Detection of after-discharge can be done in any manner referenced herein.

If the after discharge check 856 indicates an after discharge event is detected, processing proceeds to turn 848 stim off (if stimulation has not already been turned off) and continue processing with steps 850-854 in the aforementioned manner. On the other hand, if an after discharge event is not detected during the after discharge check 856, a check 858 is performed based on the sensed bioelectrical activity to determine whether suppression is indicated. This check may be performed in any of the ways discussed herein. For instance, a parameter of a sensed LFP signal and/or spectrogram may be compared to a minimum threshold representing the least amount of suppression deemed suitable before the stimulation cycle is resumed. When the parameter of the sensed 808 LFP signal and/or spectrogram rises above the minimum threshold, as is expected to end the washout period, then the suppression check 858 can determine that the suppression has subsided and the delivery of electrical stimulation can be started 842 for another stimulation cycle. Otherwise, if suppression has not subsided, processing continues to check 854, where the bioelectric activity is again sensed.

Returning now to the after discharge check 846, if an after discharge event is not detected during this check, a check 862 is made to determine whether the stim cycle timer has expired. The stim cycle timer determines how long stimulation will be provided to the patient in the absence of detection of an after discharge event. If the stim cycle times has not expired, processing continues to check 846 where it is again determined whether the patient has experienced an after discharge event. Processing based on the outcome of this check continues in the above-discussed manner. If, however, the stim cycle time has expired 862, processing continues to step 864 wherein stimulation is turned off. Also at this time, a stim off timer may be started to keep track of the amount of time the stimulation is turned off.

Next, another check 866 is then performed to determine whether an after discharge event has occurred. If so, processing continues to step 848 where stimulation is turned off (if it hasn't already been turned off) and processing continues in a manner previously described. If an after discharge event has not occurred, check 868 is performed to determine whether the stim off timer has expired. If not, processing returns to check 866 where it is again determined whether an after discharge event occurred so that appropriate action may be taken in the above-described manner.

If the off cycle timer expires as detected by check 868, processing continues to check 870 where it is determined whether suppression has been achieved. As discussed above, suppression check 870 may determine whether the bioelectrical activity level has decreased below some previously set baseline. Brain activity suppression from stimulation may be identified in various ways. As merely one example, a 20% decrease in the measure of brain activity from the baseline during sensing could indicate suppression due to the delivery of electrical stimulation. Depending on the predetermined amount of change from baseline that is desired (e.g., 20%, 50%, or other amount), suppression check 870 may be passed if sufficient suppression is identified.

If the predetermined amount of change from baseline is not detected during and/or following delivery of electrical stimulation, then the method 840 may perform a check 872 to determine whether the current stimulation parameters are below the ceiling stimulation levels beyond which stimulation levels may not be increased in some examples. Such ceiling levels may be selected prior to start of method 840, for instance. If stimulation parameter(s) are below the ceiling, an indication may be provided 874 that a stimulation energy parameter (or in some examples, multiple stimulation energy parameters) is to be increased. Such an indication may involve, for instance, setting a flag that indicates that when stimulation is again turned on, one or more stimulation energy parameters should be increased. In a particular embodiment, the setting of this flag may indicate that when stimulation is resumed, one or more stimulation parameters should be increased by some amount that may be either a predetermined amount or a dynamically determined amount (e.g., as may be determined by monitored bioelectric signals). Alternatively, the indication recorded in step 874 may be the actual values for one or more stimulation parameters that will be used when stimulation is again initiated. Stimulation may then be started 842 according to the adjusted stimulation parameter value indicated by step 874.

Returning to check 872, if the stimulation energy parameter(s) in use when stimulation was turned off were not below the determined ceiling levels, a ceiling unlock 880 check may be performed to determine whether a stimulation energy parameter should be allowed to be increased beyond the ceiling level. The outcome of the ceiling unlock 880 check may be based on a variety of factors. In some cases, the outcome of this check may be patient-specific, condition-specific, or disease-state-specific. For instance, for certain patients, patient conditions, or disease states, it may be undesirable to allow the stimulation parameter values from being increased above the ceiling level. Such patients may, for instance, be particularly susceptible to experiencing after discharge events or other adverse effects when stimulation energy parameters are increased beyond some preset ceiling levels. In other cases, it may be beneficial to allow stimulation parameter levels to be dynamically increased even about the ceiling level after stimulation is started. For instance, some patients, conditions, or disease states may be associated with an increased ability to tolerate higher levels of stimulation energy over time, and in such cases, it may be beneficial to increase stimulation levels above the ceiling over time. In some embodiments, rules may be associated with check 880 that indicate, for a particular patient, disease state, condition, etc., when and by how a ceiling may be exceeded.

If the ceiling unlock check 880 indicates the stimulation energy parameter(s) is not to be increased beyond the ceiling, processing continues to step 842 where stimulation is started without increasing the stimulation energy parameter(s). However, if check 880 indicates it is beneficial to unlock the ceiling, processing continues to step 874 wherein one or more stimulation energy parameters may be increased above the ceiling.

It is noted that any and all of the steps and options discussed in connection with FIG. 8B, or otherwise discussed herein, can be performed automatically by a medical device. For example, control circuitry of an implantable medical device may be configured to perform the steps of the method 840 of FIG. 8B.

In some cases, the methods for detecting suppression and after-discharge thresholds, identifying a suppression window, and setting therapy parameters can be repeated for awake and sleep states. It is possible that the suppression and after-discharge thresholds, or at least what will be tolerated in the awake and sleep states, will be different between the awake and sleep states. Therapy could be automatically changed between awake and sleep states, such as using therapy parameters that are based on a first suppression window associated with an awake state when the patient is awake and using therapy parameters that are based on a second suppression window associated with a sleep state when the patient is sleep. Awake and sleep states can be automatically be detected. Different electrode and electrode combinations could also be selected for therapy delivery, as discussed herein, for use during the awake and sleep states.

In various embodiments, multiple tests can be performed (e.g., the methods of FIGS. 3 and 4) for each of a cycled therapy regimen and a continuous therapy regimen to determine whether either of them is associated with a lower suppression threshold, a wider suppression window, and/or less after-discharge episodes. Such tests can also be performed for different electrode and/or electrode combinations for stimulation. A cycled or continuous therapy regimen can then be selected for therapy delivery based on which cycled or continuous mode (and further electrode or electrode combination) is associated with the lowest suppression threshold, widest suppression window, and/or lowest incidence of after-discharge episodes.

It is noted that the data presented herein concerns hippocampal stimulation and sensing. The hippocampus is a common area of seizure focus, but other areas of the brain can also be a seizure focus. The hippocampus can also be associated with other disease conditions. Accordingly, while the hippocampus is used to demonstrate various embodiments of this disclosure, the scope of this disclosure and various embodiments presented herein are not limited to sensing bioelectrical activity of the hippocampus and/or stimulation of the hippocampus, as other brain targets can be used with the embodiments disclosed herein.

Targets for stimulation and/or sensing a bioelectrical response to the stimulation for addressing a neurological condition can be in, but are not limited to, the cortex, including, but not limited to, the temporal cortex, occipital cortex, parietal cortex, frontal cortex, and entorhinal cortex. Targets for sensing and/or stimulation may not be limited to particular areas, but rather may be directed to functionally connected circuits of the brain, such along the Circuit of Papez. The areas of the brain within the Circuit of Papez are believed to be involved in the generation and spread of seizure activity. The Circuit of Papez is one of the major pathways of the limbic system, and the regions of brain within the Circuit of Papez includes the anterior nucleus, internal capsule, cingulate, hippocampus, fornix, entorhinal cortex, mammillary bodies, and mammillothalamic tract. The areas of the brain within the Circuit of Papez may be considered to be functionally connected, such that activity within one part of the Circuit of Papez may affect activity within another part of the Circuit of Papez. In this way, the delivery of stimulation to one area (e.g., the anterior nucleus) of the Circuit of Papez may affect the brain activity level within another area of the Circuit of Papez (e.g., the hippocampus).

The embodiments referenced herein, including those of FIGS. 3-10, could be used for sensing bioelectrical activity of a first brain area to determine a baseline level of activity of the first brain area, delivering electrical stimulation to a second brain area while sensing a bioelectrical response of the first brain area to the stimulation and while systematically changing a stimulation parameter, and identifying a suppression window based on the bioelectrical response of the first brain area. The suppression window can then be used for therapy delivery. In some embodiments, the first and the second brain areas are the same brain area (e.g., the hippocampus or other brain structure). In some other embodiments, the first and the second brain areas are not the same brain area. For example, the first brain area (i.e. the area targeted for sensing) may be the anterior nucleus while the second brain area (i.e. the area targeted for stimulation) may be the hippocampus. The first brain area (i.e. the area targeted for sensing) and the second brain area (i.e. the area targeted for stimulation) may each be different areas of the cortex. In some embodiments, the second brain area is stimulated by a remote lead that does not directly stimulate the second brain area (e.g., a lead located along the Circuit of Papez such as in the anterior nucleus to stimulate the hippocampus as the second brain area) while a remote lead or a lead local to the first brain area (e.g., the hippocampus) senses a bioelectrical response to the remote stimulation of the second brain area. Based on the bioelectrical responses, suppression and after-discharge thresholds can be determined and a suppression window can be identified as discussed herein. The suppression window can then be used for therapy delivery.

While the techniques discussed herein are particularly suited for treatment of temporal lobe epilepsy, the techniques discussed herein can be used to address other conditions. Several disease conditions are associated with abnormal levels of bioelectrical activity in the cortex of the brain, such as some seizure conditions. As such, multiple different disease conditions could potentially benefit from a therapy as described herein. For example, stimulation to suppress bioelectrical activity may be therapeutic in disease conditions associated with abnormal levels (e.g., abnormally high or erratic) of bioelectrical activity. Moreover, suppression and after-discharges can be produced in various brain areas, including cortical areas. As such, the embodiments referenced herein may be applicable to any brain stimulation therapy to reduce or otherwise change some aspect of bioelectrical activity while avoiding after-discharges. Various embodiments referenced herein could be used to reduce symptoms of Alzheimer's disease or improve the memory and/or concentration functions of a patient suffering from a neurological condition. Embodiments of this disclosure could be used to treat symptoms of movement disorders including without limitation Parkinson's disease, dystonia, tremor, and akinesia. Embodiments of this disclosure could be used to treat symptoms of disorders including without limitation depression, schizophrenia, addiction, sleep dysfunction, obsessive compulsive disorder, and obesity.

As such, control circuitry can be configured to automatically implement the methods of FIGS. 3-8B or otherwise referenced herein to treat conditions other than seizure condition and/or target areas other than the hippocampus for sensing and/or stimulation.

In various embodiments, a report can be made detailing bioelectrical response information. Bioelectrical response information may be collected by an implanted device (e.g., an implanted device implementing the methods of any of FIGS. 3-8), transmitted externally, and the displayed in a report by an external programmer or other device. Various embodiments may store event data, such as the episodes of successful suppression by stimulation, failure of stimulation to suppress bioelectrical activity, and/or after-discharges. Such data may be collected while an implanted device operates according to any embodiment, such as any of FIGS. 3-8. Metrics that can be calculated and provided as a report based on sensed data can include, but are not limited to, the number of stimulation cycles in which an after-discharge was provoked, severity of after-discharges (e.g., the average RMS, spectral energy, or other parameter reflecting the bioelectrical intensity of a plurality of after-discharges), average degree of suppression from baseline, time spent in a suppressed state (e.g., total time, percentage of time, average duration of a suppression state), average of how long it takes a stimulation cycle to provoke an after-discharge (e.g., average time from the start of stimulation until an after-discharge is provoked), and/or number of patient seizures.

Different frequency bands are associated with different conditions, some of which are discussed herein in various examples. Generally accepted frequency bands are shown in Table 1:

TABLE 1

| Frequency (f) Band Hertz (Hz) | Frequency Information |
| --- | --- |
| f <4 Hz | δ (delta frequency band) |
| 4 Hz ☐ f ☐ 8 Hz | theta frequency band |
| 8 Hz ☐ f ☐ 13 Hz | α (alpha frequency band) |
| 13 Hz ☐ f ☐ 35 Hz | β (beta frequency band) |
| 35 Hz ☐ f ☐ 100 Hz | γ (gamma frequency band) |
| 100 Hz ☐ f ☐ 200 Hz | high γ (high gamma frequency band) |

Although various embodiments presented herein concern the provoking of an after-discharge to set stimulation parameters, some embodiments will only scan a stimulation parameter to determine a baseline of bioelectrical activity and a suppression threshold. For example, a device may be configured to monitor bioelectrical activity until a baseline level can be identified and then a simulation parameter can be increased while the device senses until suppression is detected. A stimulation parameter for therapy delivery can then be set at or some predetermined amount above the suppression threshold. The therapy can then be delivered. The device may monitor bioelectrical activity during therapy delivery to confirm suppression and make delivery adjustments if suppression is lost and/or stop therapy or decrease stimulation intensity if an after-discharge is detected (e.g., as in FIGS. 6-8).

Returning to the spectrogram 102 of FIG. 1, it is noted that a pronounced band of activity in the theta frequency band persisted throughout testing, and during other times when the subjects were awake. This theta frequency band was significantly diminished when the subjects were not awake (e.g., during anesthetized states). The balance between excitatory and inhibitory drive within this network is likely very different under these two behavioral conditions. As such, detection of a theta band can be used to detect various patient states. For example, an implantable medical device could automatically detect awake states based on theta band power above a threshold and detect non-awake states (e.g., a sleep state) based on theta band power above a threshold. The theta band energy could be sensed from the hippocampus via a lead in the hippocampus.

Different therapy parameters may be used for therapy delivery based on the relative presence or absence of theta band activity. For example, different stimulation parameters can be used for awake and sleep states, as discussed above based on different suppression windows based on sleep and awake states, and a switch between awake and sleep parameters can automatically be triggered based on theta band activity being above or below a threshold. However, awake and sleep state detection can be implemented independently of these therapy changes, and could be used alone or used to automatically implement other therapy changes based on awake and sleep states.

It is noted that this disclosure refers to embodiments for identifying a suppression window and using the suppression window for therapy delivery. Suppression might refer to abolishing or reducing a signature of an undesirable brain state. While the data of FIG. 1 specifically concerns producing a stimulation effect in a subject, other therapeutic effects could additionally or alternatively be produced while avoiding after-discharge events. In some cases, producing a stimulation effect could be understood as changing a brain state. As such, each reference herein to suppression could instead reference changing a brain state relative to a previous brain state (e.g., for which the brain state to which the brain changed might not necessarily be suppression relative to a previous brain state). The previous brain state may be an unwanted brain state having a bioelectrical signature and be associated with a neurological condition. Changing of the brain state by stimulation may comprise reducing, eliminating, or otherwise changing the occurrence of the bioelectrical signature. In any case, the embodiments described herein (e.g., FIGS. 3-8) could be modified to scan a stimulation parameter, identify a window for changing a brain state based on a brain state change threshold (below which stimulation does not cause the change and above which the change is produced) and an after-discharge threshold, and then set a stimulation parameter for therapy based on the window for changing the brain state.

It is noted that not all embodiments will perform each of the steps of the methods presented herein, and modifications to the methods are contemplated, whether by omitting and/or adding steps. Each of the methods discussed herein can be fully or partially implemented in control circuitry of an implantable medical device (e.g., a neurostimulator configured for DBS) and/or an external device. In some embodiments, control circuitry may be configured to implement multiple of the methods described herein, such as profiling a patient response and/or setting stimulation parameters (e.g., as described in connection with FIGS. 1-5) and then controlling therapy delivery (e.g., as described in connection with FIGS. 6-7).

Figure 9:
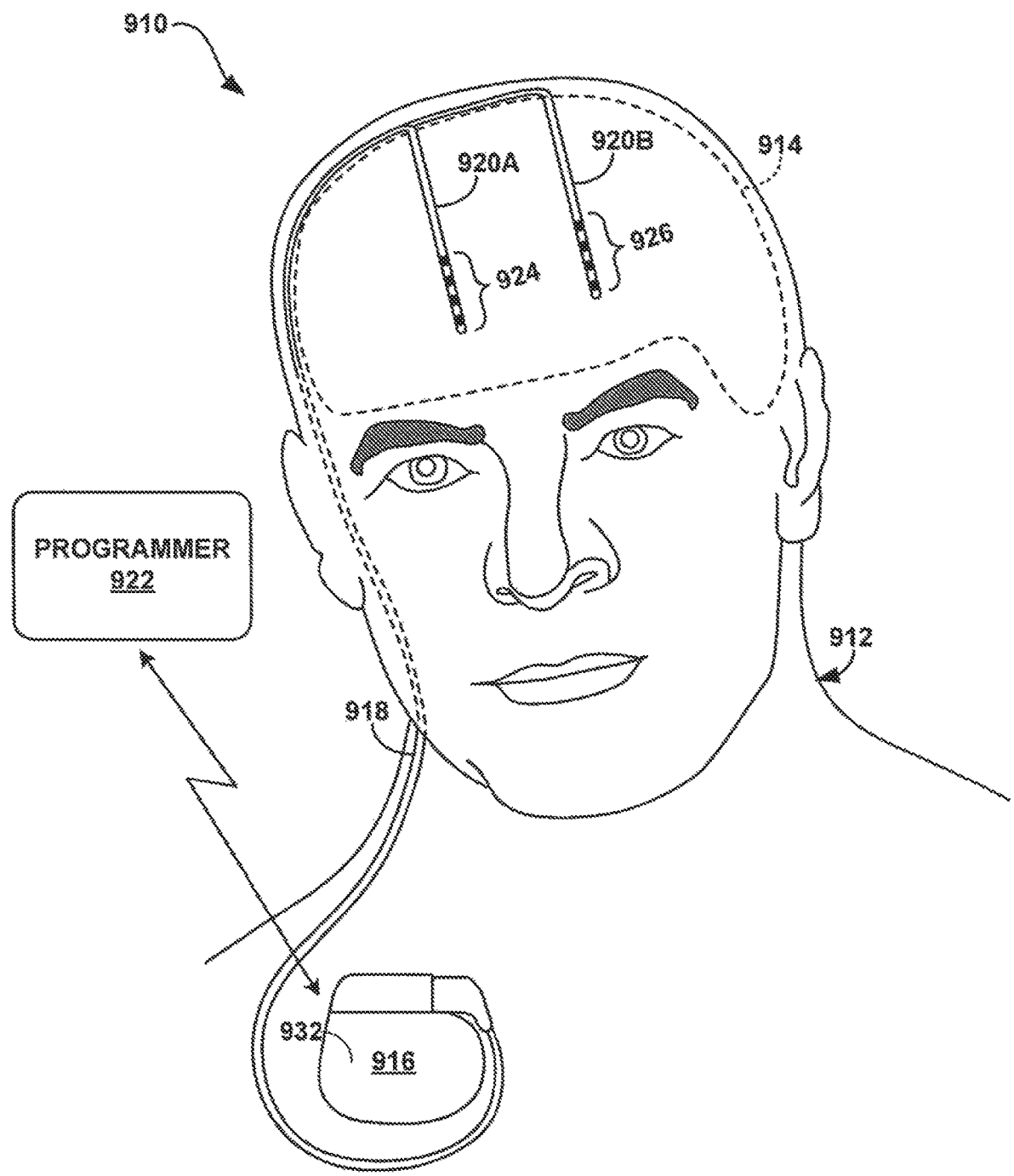
FIG. 9 is a conceptual diagram illustrating an example deep brain stimulation system for delivery of electrical stimulation to a brain of a patient.

FIG. 9 is a conceptual diagram illustrating an example therapy system 910 that delivers electrical stimulation, senses a bioelectrical response to the stimulation, monitors a brain state, and/or adjusts therapy delivery to patient 912 to manage a brain condition, among other functions described herein. System 910 includes implantable medical device (IMD) 916, lead extension 918, one or more leads 920A and 920B (collectively "leads 920") with respective sets of electrodes 924, 926 and medical device programmer 922. IMD 916 may include monitoring circuitry in electrical connection with the electrodes 924, 926 of leads 920A and 920B, respectively.

System 910 may monitor one or more bioelectrical signals of patient 912. For example, IMD 916 may include a sensing module (e.g., sensing module 944 of FIG. 10) that senses bioelectrical signals of one or more areas of brain 914. In the embodiment shown in FIG. 9, the signals may be sensed by one or more electrodes 924, 926 and conducted to the sensing module within IMD 916 via conductors within the respective leads 920A, 920B. As described in further detail below, in some embodiments, control circuitry of IMD 916 or another device (e.g., programmer 922) monitors the bioelectrical signals within brain 914 of patient 912 to identify one or more biomarkers and determine a patient state, such as determine baseline bioelectrical activity, identify suppression of bioelectrical activity, identify an after-discharge episode, and/or perform the other functions referenced herein including those referenced in connection with FIGS. 1-8. Control circuitry of IMD 916 or another device (e.g., programmer 922) may analyze bioelectrical signals and/or other signals, identify bioelectrical responses and/or patient states, and/or control delivery of electrical stimulation to brain 914 in a manner that treats a brain condition of patient 912.

In some examples, the sensing module of IMD 916 may receive the bioelectrical signals from electrodes 924, 926 or other electrodes positioned to monitor bioelectrical signals of patient 912 (e.g., if housing 932 of IMD 916 is implanted in or proximate brain 914, an electrode of housing 932 can be used to sense bioelectrical signals and/or deliver stimulation to brain 914). Electrodes 924, 926 may also be used to deliver electrical stimulation from stimulation generator 942 to target sites within brain 914 as well as to sense bioelectrical signals within brain 914. However, IMD 916 can also use separate sensing electrodes to sense the bioelectrical signals. In some embodiments, the sensing module of IMD 916 may sense bioelectrical signals via one or more of the electrodes 924, 926 that are also used to deliver electrical stimulation to brain 914. In other embodiments, one or more of electrodes 924, 926 may be used to sense bioelectrical signals while one or more different electrodes 924, 926 may be used to deliver electrical stimulation.

Examples of the monitored bioelectrical signals include, but are not limited to, an EEG signal, an ECoG signal, an MEG signal, and/or a LFP signal sensed from within or about one or more locations of brain 914. These and other signals can be used to perform various functions referenced herein.

As described in further detail below, IMD 916 may deliver therapy to any suitable portion of brain 914. For example, system 910 may provide therapy to correct a brain disorder and/or manage symptoms of a neurodegenerative brain condition. Patient 912 ordinarily will be a human patient. In some cases, however, system 910 may be applied to other mammalian or non-mammalian non-human patients.

IMD 916 may include a module that includes a stimulation generator 942 that generates and delivers electrical stimulation therapy to one or more regions of brain 914 of patient 912 via the electrodes 924, 926 of leads 920A and 920B, respectively. In the example shown in FIG. 9, system 910 may be referred to as deep brain stimulation system because IMD 916 may provide electrical stimulation therapy directly to tissue within brain 914, e.g., a tissue site under the dura mater of brain 914. In some other embodiments, leads 920 may be positioned to sense brain activity and/or deliver therapy to a surface of brain 914, such as the cortical surface of brain 914, or other location in or along the patient 912.

In the example shown in FIG. 9, IMD 916 may be implanted within a subcutaneous pocket below the clavicle of patient 912. In other embodiments, IMD 916 may be implanted within other regions of patient 912, such as a subcutaneous pocket in the abdomen or buttocks of patient 912 or proximate the cranium of patient 912. Implanted lead extension 918 is coupled to IMD 916 via a connector block (also referred to as a header), which may include, for example, electrical contacts that electrically couple to respective electrical contacts on lead extension 918. The electrical contacts electrically couple the electrodes 924, 926 carried by leads 920 to IMD 916. Lead extension 918 traverses from the implant site of IMD 916 within a chest cavity of patient 912, along the neck of patient 912 and through the cranium of patient 912 to access brain 914. Generally, IMD 916 is constructed of a biocompatible material that resists corrosion and degradation from bodily fluids. IMD 916 may comprise a hermetic housing 932 to substantially enclose control circuitry components, such as a processor, sensing module, therapy module, and memory. In some implementations, IMD 916 and other components (e.g., leads 920) may be implanted only in the head of the patient (e.g., under the scalp) and not in the chest and neck regions.

Electrical stimulation may be delivered to one or more areas of brain 914, which may be selected based on many factors, such as the type of patient condition for which system 910 is implemented to manage. In some cases, leads 920 may be implanted within the right and left hemispheres of brain 914 (e.g., as illustrated in FIG. 9) while, in other examples, one or both of leads 920 may be implanted within one of the right or left hemispheres. Other implant sites for leads 920 and IMD 916 are contemplated. For example, in some examples, IMD 916 may be implanted on or within cranium. In addition, in some examples, leads 920 may be coupled to a single lead that is implanted within one hemisphere of brain 914 or implanted through both right and left hemispheres of brain 914.

Leads 920 may be positioned to deliver electrical stimulation to one or more target tissue sites within brain 914 to manage patient symptoms associated with a disorder of patient 912. Tissue targeted for stimulation may be the same tissue that generates the monitored bioelectrical activity (e.g., the activity which therapy attempts to suppress). However, in some cases the tissue targeted for stimulation will be different from the tissue which generates the bioelectrical activity being monitored. Leads 920 may be implanted to position electrodes 924, 926 at desired locations of brain 914 through respective holes in cranium. Leads 920 may be placed at any location(s) within or along brain 914 such that electrodes 924, 926 are capable of providing electrical stimulation to target tissue sites of brain 914 during treatment and/or proximate tissue being monitored. In some embodiments, leads may be placed such that electrodes 924, 926 directly contact or are proximate tissue targeted for stimulation and/or monitoring.

In the example shown in FIG. 9, electrodes 924, 926 of leads 920 are shown as ring electrodes. Ring electrodes are typically capable of sensing and/or delivering an electrical field to any tissue adjacent to leads 920 (e.g., in all directions away from an outer perimeter of leads 920). In other examples, electrodes 924, 926 of leads 920 may have different configurations. For example, electrodes 924, 926 of leads 920 may have a complex electrode array geometry that is capable of producing shaped electrical fields. The complex electrode array geometry may include multiple electrodes (e.g., partial ring or segmented electrodes) around the perimeter of each lead 920, rather than a ring electrode. In this manner, electrical brain sensing and/or electrical stimulation may be associated with a specific direction from leads 920 (e.g., less than the entire outer perimeter of leads 920) to enhance direction sensing and/or therapy efficacy and reduce possible adverse side effects from stimulating a large volume of tissue in the case of stimulation. As such, electrodes can be positioned to preferentially sense from one side of a lead and to stimulate targeted tissue and avoid stimulating non-targeted tissue. In examples, leads 920 may have shapes other than elongated cylinders as shown in FIG. 9. For example, leads 920 may be paddle leads, spherical leads, bendable leads, or any other type of shape effective in treating patient 912.

In some embodiments, outer housing 932 of IMD 916 may include one or more stimulation and/or sensing electrodes. For example, housing 932 can comprise an electrically conductive material that is exposed to tissue of patient 912 (e.g., the can containing circuitry being electrical connected to sensing and/or stimulation circuitry) when IMD 916 is implanted in patient 912, or an electrode can be attached to housing 932.

In some examples, the location of the electrodes 924, 926 within brain 914 can be determined based on analysis of a bioelectrical signal of the patient sensed via one or more of the electrodes 924, 926. For example, a particular physiological structure (e.g., the amygdala) may exhibit a unique electrical signal and, thus, facilitate positioning of the electrodes of the lead at the desired implant location through monitoring of the bioelectrical signal.

Leads 920 may be implanted within a desired location of brain 914 via any suitable technique, such as through respective burr holes in a skull of patient 912 or through a common burr hole in the cranium. Leads 920 may be placed at any location within brain 914 such that electrodes 924, 926 of leads 920 are capable of sensing electrical activity of the brain areas and/or providing electrical stimulation to targeted tissue for treatment.

In some embodiments, a processor of system 910 (e.g., a processor of programmer 922 or IMD 916) controls delivery of electrical stimulation by activating electrical stimulation, deactivating electrical stimulation, increasing the intensity of electrical stimulation, or decreasing the intensity of electrical stimulation delivered to brain 914 to titrate electrical stimulation therapy. In this way, therapy can be started, stopped, and/or changed by a processor in any manner and based on any parameter or finding as discussed herein.

System 910 may also store a plurality of stimulation programs (e.g., a set of electrical stimulation parameter values). A processor of IMD 916 or programmer 922 may select a stored stimulation program that defines electrical stimulation parameter values for delivery of electrical stimulation to brain 914 based on a characterization of neural activation. Where IMD 916 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The therapy may be characterized by stimulation delivery settings based on a patient response profile, such as using stimulation parameters within a suppression window or otherwise determined by the embodiments referenced herein (e.g., as discussed in connection with FIGS. 1-8).

External programmer 922 wirelessly communicates with IMD 916 as needed to provide or retrieve information. For example, external programmer 922 may receive sensed data and/or information from IMD 916, as well as send therapy program information to IMD 916. Programmer 922 is an external computing device that the user, e.g., the clinician and/or patient 912, may use to communicate with IMD 916. For example, programmer 922 may be a clinician programmer that the clinician uses to communicate with IMD 916 and program one or more therapy programs for IMD 916. Additionally or alternatively, programmer 922 may be a patient programmer that allows patient 912 to input information (e.g., a self-evaluated assessment regarding symptoms and/or patient state), select programs, and/or view and modify therapy parameters. In some embodiments, a programmer 922 can display a patient profile showing a suppression threshold, an after-discharge threshold, data (e.g., the plots of FIG. 1), a response profile (e.g., the response profile of FIG. 2), a log of detected events, and/or any other information referenced herein.

Programmer 922 is a medical device that may be a hand-held computing device with a display viewable by the user and an interface for providing input to programmer 922 (i.e., a user input mechanism) and/or displaying information received from the IMD 916. For example, programmer 922 may include a small display screen (e.g., a liquid crystal display (LCD) or a light emitting diode (LED) display) that presents information to the user. In addition, programmer 922 may include a touch screen display, keypad, buttons, a peripheral pointing device or another input mechanism that allows the user to navigate through the user interface of programmer 922 and provide input. A screen (not shown) of programmer 922 may be a touch screen that allows the user to provide input directly to the user interface shown on the display. The user may use a stylus or finger to provide input to the display, such as an indication that the patient is in a particular patient state as part of a training phase as discussed herein.

In various embodiments, programmer 922 is a medical device that may be a larger workstation or a separate application within another multi-function device, rather than a dedicated computing device. For example, the multi-function device may be a notebook computer, tablet computer, workstation, cellular phone, personal digital assistant or another computing device. The circuitry components of a programmer and/or other external device(s), such as equivalent circuitry to that of FIG. 10, can be control circuitry as means for performing functions as described herein (e.g., determining a bioelectrical response to stimulation and/or changing a therapy), including those described in association with FIGS. 1-8. Various embodiments of external circuitry may include a screen on which information can be presented. The output of a screen may be controlled by control circuitry.

When programmer 922 is configured for use by the clinician, programmer 922 may be used to transmit initial programming information to IMD 916. This initial information may include hardware information, such as the type of leads 920, the arrangement of electrodes 924, 926 on leads 920, the position of leads 920 within brain 914, initial programs defining therapy parameter values, and any other information that may be useful for programming into IMD 916. Programmer 922 may also be capable of controlling circuitry of the IMD 916 in carrying out the functions described herein.

The clinician may also store therapy programs within IMD 916 with the aid of programmer 922. During a programming session, the clinician may determine one or more stimulation programs that may effectively bring about a therapeutic outcome that treats a brain condition, such with as the therapy parameter setting techniques of FIGS. 3-5. During the programming session, the clinician may evaluate the efficacy of the one or more stimulation settings (e.g., pulse amplitude, pulse width, pulse frequency, and a resultant bioelectrical response) based on one or more findings of a sensed signal. In some examples, programmer 922 may assist the clinician in the creation/identification of stimulation programs by providing a methodical system for identifying potentially effective stimulation parameter values, such as by recommending stimulation parameters within a suppression window and/or using an electrode(s) associated with the lowest suppression threshold. In some examples, the processor of programmer 922 may calculate and display one or more therapy metrics for evaluating and comparing therapy programs available for delivery of therapy from IMD 916 to patient.

Programmer 922 may also provide an indication to patient 912 when therapy is being delivered which may aid the assessment of therapy efficacy. For example, concurrent with or following the delivery of electrical stimulation, the patient may evaluate whether he or she seems to have symptoms (e.g., of a seizure) by answering questions presented on the programmer 922 corresponding to times when baseline bioelectrical activity levels are sensed, when suppression is detected, during an after-discharge, and/or during a washout period. The information may be used to determine the relationship between stimulation intensity and a bioelectrical response, such as in the training phase of FIG. 5.

Whether programmer 922 is configured for clinician or patient use, programmer 922 may be configured to communicate with IMD 916 and, optionally, another computing device, via wireless communication. Programmer 922, for example, may communicate via wireless communication with IMD 916 using telemetry techniques known in the art, including inductive telemetry, arm's-length telemetry, and longer-range telemetry. Programmer 922 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 922 may also communicate with other programming or computing devices via exchange of removable media, such as magnetic or optical disks, memory cards or memory sticks. Further, programmer 922 may communicate with IMD 916 and another programmer via remote telemetry techniques known in the art, communicating via a local area network (LAN), wide area network (WAN), public switched telephone network (PSTN), or cellular telephone network, for example.

Figure 10:
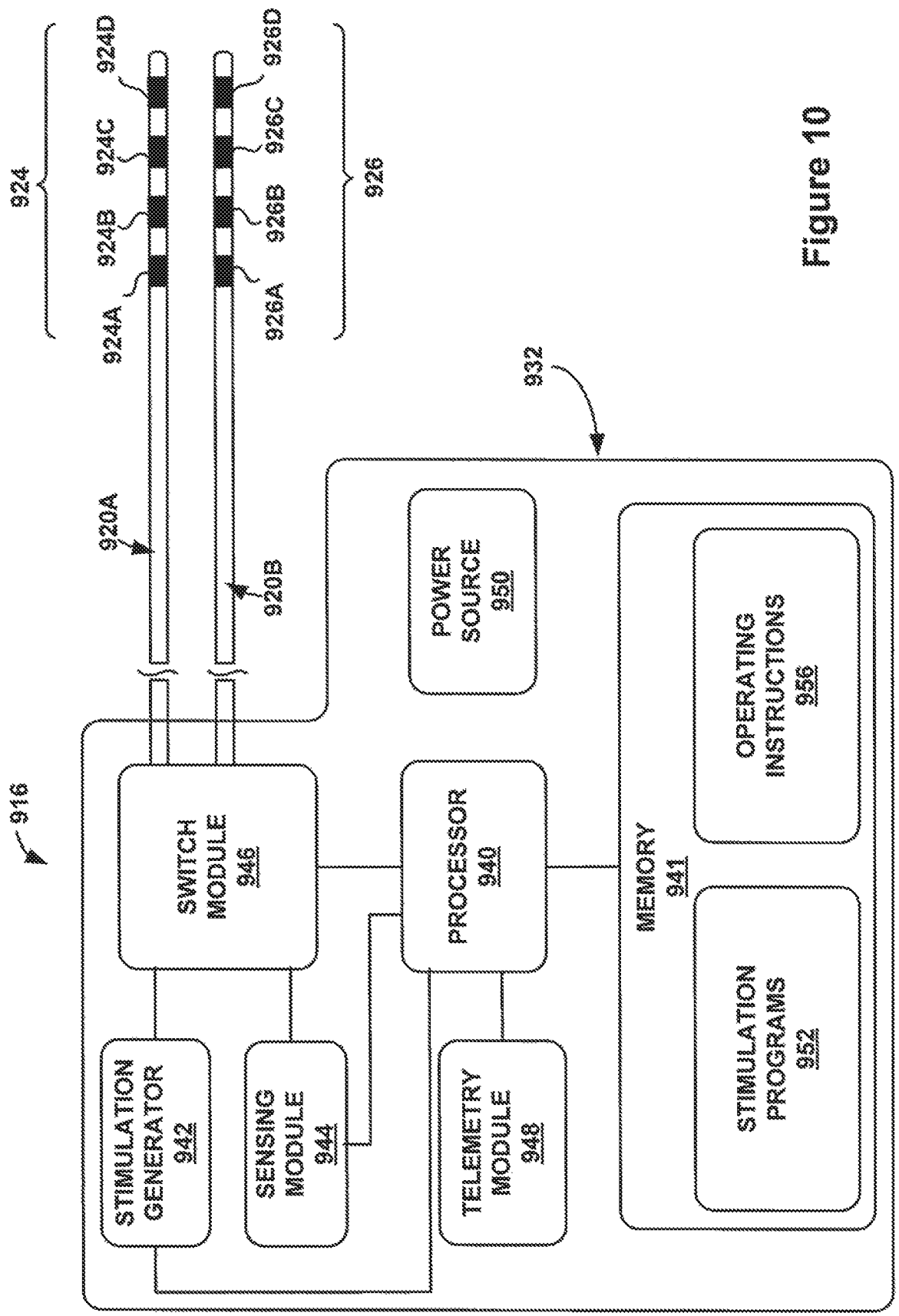
FIG. 10 is a conceptual diagram illustrating an example therapy system for delivery of electrical stimulation to a brain of a patient.

FIG. 10 is a functional block diagram illustrating components of IMD 916. In the configuration shown in FIG. 10, IMD 916 includes processor 940, memory 941, stimulation generator 942, and sensing module 944, which can be control circuitry as means for performing functions as described herein (e.g., delivering stimulation, sensing a brain signal, determining a bioelectrical response to the stimulation from the signal, and administering therapy based on the response and/or any of the techniques referenced in connection with FIG. 1-8). Memory 941 may include any volatile or non-volatile media, such as a random access memory (RAM), read only memory (ROM), non-volatile RAM (NVRAM), electrically erasable programmable ROM (EEPROM), flash memory, and the like. Memory 941 may store computer-readable instructions that, when executed by processor 940, cause IMD 916 to perform various functions described herein. Memory 941 may include operating instructions 956 executable by the processor 940 for causing the IMD 916 to carry out the various functions referenced herein, including those discussed in association with FIGS. 1-8. Memory 941 may store therapy instructions as part of stimulation programs 952 that are available to be selected by processor 940 in response to particular conditions (e.g., no suppression, suppression, after-discharge) detected by the sensing module 944 or determination of a particular patient state. In addition, processor 940 may be configured to record diagnostic information, such as sensed signals, measured values, detected events, biomarker signatures, patient state episode information, and the like in memory 941 or another memory or storage device. The various functions and techniques described herein may be performable automatically by the IMD 916 by processor 940 execution of operating instructions 956 and stimulation programs 952 stored in memory 941.

The steps, procedures, techniques, etc. referenced herein may be carried out in part by, for example, software or firmware instructions, such as those used to define a software or computer program. The non-transitory computer-readable medium (e.g., memory 941) may store instructions (e.g., operating instructions 956 and stimulation programs 952) executable by a processor (e.g., processor 940 and/or of an external device) to carry out the steps, procedures, techniques, etc. In this way, control circuitry can be configured to perform the various steps, procedures, techniques, etc. as described herein, including those discussed in association with FIGS. 1-8. The computer-readable medium may be a computer-readable storage medium such as a storage device (e.g., a disk drive, or an optical drive), memory (e.g., a Flash memory, random access memory or RAM) or any other type of volatile or non-volatile memory that stores processor executable instructions (e.g., in the form of a computer program or other executable) as part of control circuitry to carry out the functions described herein.

Processor 940 may be configured to cause stimulation generator 942 to deliver electrical stimulation with pulse voltage or current amplitudes, pulse widths, and frequencies (i.e., pulse rates) as part of control circuitry, and electrode combinations specified by the stimulation programs 952, e.g., as stored in memory 941. Processor 940 may control stimulation generator 942 to deliver each pulse, or a group of pulses, according to a different program of the stimulation programs, such that multiple programs of stimulation are delivered on an interleaved or alternating basis, e.g., having different delays or responding to different biomarkers, bioelectrical responses, or patient states. In some embodiments, processor 940 may control stimulation generator 942 to deliver a substantially continuous stimulation waveform rather than pulsed stimulation.

As shown, the set of electrodes 924 of lead 920A includes electrodes 924A, 924B, 924C, and 924D, and the set of electrodes 926 of lead 920B includes electrodes 926A, 926B, 926C, and 926D. Processor 940 may control switch module 946 to route sensed signals to sensing module 944 and/or apply the stimulation signals generated by stimulation generator 942 to selected combinations of electrodes 924, 926. In particular, switch module 946 may couple stimulation signals to selected conductors within leads 920, which, in turn, deliver the stimulation signals across selected electrodes 924, 926. Switch module 946 may be a switch array, switch matrix, multiplexer, or any other type of switching module configured to selectively couple stimulation energy to selected electrodes 924, 926 and to selectively sense bioelectrical signals with selected electrodes 924, 926. Hence, stimulation generator 942 is coupled to electrodes 924, 926 via switch module 946 and conductors within leads 920. In some embodiments, however, IMD 916 does not include switch module 946.

Sensing module 944 is configured to sense bioelectrical signals of patient 912 via a selected subset of one or more electrodes 924, 926, or with one or more electrodes 924, 926 and at least a portion of a conductive outer housing 932 of IMD 916, an electrode on an outer housing of IMD 916, or another reference. In some embodiments, sensing module 944 may measure the amplitude of a signal and relate the value to processor 940. Processor 940 may control switch module 946 to electrically connect sensing module 944 to selected electrodes 924, 926. In this way, sensing module 944 may selectively sense bioelectrical signals with different combinations of electrodes 924, 926 (and/or a reference other than an electrode 924, 926). Although the electrodes 924, 926 are principally described as being implanted within a brain in the manner of DBS, other locations are additionally or alternatively contemplated. For example, electrodes may be deployed at selected tissue sites or on selected surfaces of a human patient, such as on the brain, along the cortex, proximate the spinal cord, on the scalp, or elsewhere. As an example, scalp electrodes may be used to measure or record EEG signals. As another example, electrodes implanted at the surface of the cortex may be used to measure or record ECoG signals. In some embodiments, an external device may be worn with sensing elements positioned at a desired location adjacent the patient to detect a bioelectrical signal.

Sensing module 944 may form part of a sensor circuit configured to monitor a variety of signals via a variety of different sensing elements, such as a bioelectrical signal via electrodes 924, 926, and/or other physiological signals. Sensing module 944 may include amplifiers, filters, modulators, and other circuitry for conditioning and measuring one or more parameters of signals. Sensing module 944 and/or processor 940 (and/or other circuitry) may condition one or more sensed signals to account for noise and/or identify a bioelectrical response according to any technique referenced herein. In some embodiments, sensing module 944 may directly process signals obtained from electrodes 924, 926 or other sensing elements with little or no preprocessing by other components. In other embodiments, sensing module 944 may include preprocessing circuitry to process or convert signals for analysis by processor 940 or other circuitry. In some embodiments, sensing module 944 includes circuitry configured to measure one or more parameters of an electrical signal, such as amplitude, and processor 940 receives an output from the telemetry module 948 of an indication of the measurement for further analysis as discussed herein, such as extracting spectral characteristics of the signal and/or determining a bioelectrical response to stimulation. Such circuitry may further discriminate which one of a plurality of different states.

A sensing module 944 that includes a circuit architecture that directly extracts energy in key frequency bands of a bioelectrical brain signal may be useful for tracking the power fluctuations within the selected frequency bands and determining a bioelectrical response to stimulation based on the bioelectrical brain signal. In some examples, the energy in particular frequency band or bands of a bioelectrical signal may be used as a parameter that serves as a feature value in a supervised learning algorithm, such as an support vector algorithm or an support vector machine-based classification algorithm generated based on the support vector machine algorithm.

Stimulation generator 942, under the control of processor 940, generates stimulation signals for delivery to patient 912 via selected combinations of electrodes 924, 926. Processor 940 controls stimulation generator 942 according to stimulation programs 952 stored in memory 941 to apply particular stimulation parameter values specified by one or more programs, such as amplitude, pulse width, timing, and pulse rate. The stimulation programs 952 may also specify the timing of stimulation, such as the timing of stimulation according to a cycled stimulation regimen. In various embodiments, stimulation generator 942 generates and delivers stimulation signals to one or more target portions of brain 914 via a select combination of electrodes 924, 926.

Although sensing module 944 is incorporated into a common housing 932 with stimulation generator 942 and processor 940, in other examples, sensing module 944 is in a physically separate outer housing from outer housing 932 of IMD 916 and communicates with processor 940 via wired or wireless communication techniques.

Telemetry module 948 supports wireless communication between IMD 916 and an external programmer 922 or another computing device under the control of processor 940. Processor 940 of IMD 916 may receive, as updates to sensing and/or stimulation programs, information concerning the therapy programs, thresholds, and/or values for stimulation parameters for delivering therapy from programmer 922 via telemetry module 948. The updates to the stimulation, sensing, or other programs may be stored within stimulation programs 952 or other section of memory 941. Telemetry module 948 in IMD 916, as well as telemetry modules in other devices and systems described herein, such as programmer 922, may accomplish communication by RF communication and/or inductance techniques, among other transcutaneous communication techniques. For example, telemetry module 948 may communicate with external medical device programmer 922 via proximal inductive interaction of IMD 916 with programmer 922. Accordingly, telemetry module 948 may send information to external programmer 922 on a continuous basis, at periodic intervals, or upon request from IMD 916 or programmer 922. For example, processor 940 may transmit sensed signals, biomarker identification information, episodic information, stimulation history information, and/or information concerning a profile of a patient's bioelectrical response to stimulation to programmer 922 via telemetry module 948.

Power source 950 delivers operating power to various components of IMD 916. Power source 950 may include a small rechargeable or non-rechargeable battery and a power generation circuit to produce the operating power. Recharging may be accomplished through proximal inductive interaction between an external charger and an inductive charging coil within IMD 916. In various embodiments, traditional batteries may be used.

The techniques described in this disclosure, including those attributed to programmer 922, IMD 916, processor, control circuitry or various constituent components, may be implemented, at least in part, in hardware, software, firmware or any combination thereof. Such hardware, software, firmware may be implemented within the same device or within separate devices to support the various operations and functions described in this disclosure. While the techniques described herein are primarily described as being performed by processor 940 of IMD 916 and/or processor of a programmer or other external device as part of control circuitry, any of the one or more parts of the techniques described herein may be implemented by a processor of one of IMD 916, programmer 922, or another computing device, alone or in combination with each other, as control circuitry. For example, the various functional options discussed in connection with FIGS. 1-8 and elsewhere herein can be implemented by a processor (e.g., processor 940) executing program instruction stored in memory (e.g., memory 941), as control circuitry, that performs the various described functions.

Although the control circuitry of FIG. 10 is generally illustrated and described in terms of an implantable medical device, the control circuitry could alternatively be embodied in an at least partially external device and, depending on the therapy and/or circuitry configuration, may be wholly external.

The techniques described in this disclosure, including those discussed in connection with FIGS. 1-8 and those attributed to programmer, IMD, processor, and/or control circuitry, or various constituent components, may be implemented wholly or at least in part, in hardware, software, firmware or any combination thereof. A processor, as used herein, refers to any number and/or combination of a microprocessor, a digital signal processor (DSP), an application specific integrated circuit (ASIC), a field-programmable gate array (FPGA), microcontroller, processing chip, gate arrays, and/or any other equivalent integrated or discrete logic circuitry. "Control circuitry" as used herein refers to at least one of the foregoing logic circuitry as a processor, alone or in combination with other circuitry, such as memory or other physical medium for storing instructions, as needed to carry about specified functions (e.g., a processor and memory having stored program instructions executable by the processor as control circuitry configured to carry out one or more specified functions). The functions referenced herein (e.g., those discussed in connection with FIGS. 1-8) may be embodied as firmware, hardware, software or any combination thereof as part of control circuitry specifically configured (e.g., with programming) to carry out those functions, such as in means for performing the functions referenced herein. The steps described herein may be performed by a single processing component or multiple processing components, the latter of which may be distributed amongst different coordinating devices (e.g., an IMD and an external programmer). In this way, control circuitry may be distributed between multiple devices, including an implantable medical device and an external medical device in various systems. In addition, any of the described units, modules, or components may be implemented together or separately as discrete but interoperable logic devices of control circuitry. Depiction of different features as modules or units is intended to highlight different functional aspects and does not necessarily imply that such modules or units must be realized by separate hardware or software components and/or by a single device. Rather, functionality associated with one or more module or units, as part of control circuitry, may be performed by separate hardware or software components, or integrated within common or separate hardware or software components of the control circuitry.

When implemented in software, the functionality ascribed to the systems, devices and control circuitry described in this disclosure may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of control circuitry. The instructions may be executed to support one or more aspects of the functionality described in this disclosure.

It is noted that this disclosure is presented in an exemplary format and not in a limiting manner. The scope of this disclosure is not limited to the specific embodiments presented herein. The various options shown herein can be selectively employed and modified by one having ordinary skill in the art to practice the subject matter of this disclosure.

The invention claimed is:

1. A method comprising:
controlling stimulation circuitry to deliver electrical stimulation to a brain at a plurality of different levels of a stimulation parameter;
sensing, using one or more electrodes, bioelectrical brain activity, wherein sensing the bioelectrical brain activity of the brain comprises sensing a bioelectrical response of the brain to the delivery of the electrical stimulation at each of the plurality of different levels of the stimulation parameter, wherein sensing the bioelectrical response comprises sensing an after-discharge episode resulting from the delivery of the electrical stimulation at at least one level of the plurality of different levels of the stimulation parameter;
identifying a window of the stimulation parameter having a first threshold as a lower boundary and an after-discharge threshold as an upper boundary based on the sensed bioelectrical brain activity, wherein identifying a window of the stimulation parameter based on the sensed biological brain activity comprises determining the first threshold and the after-discharge threshold of the window of the stimulation parameter based on the sensed bioelectrical activity, wherein determining the after-discharge threshold comprises determining the after discharge threshold based on the at least one level of the plurality of different levels of the stimulation parameter that resulted in the sensed after-discharge episode; and
setting a therapy level of the stimulation parameter for therapy delivery to the brain based on the window, wherein sensing, delivering, identifying, and setting are each performed at least in part by control circuitry.

2. The method of claim 1, wherein the sensing, using the one or more electrodes, the bioelectrical brain activity of the brain of the patient comprises periodically sensing, using the one or more electrodes, the bioelectrical brain activity of the brain of the patient, and
wherein the identifying the window of the stimulation parameter having the first threshold as the lower boundary and the after-discharge threshold as the upper boundary based on the sensed bioelectrical brain activity comprises periodically identifying the after-discharge threshold as the upper boundary based on the sensed bioelectrical brain activity such that the upper boundary is periodically adjusted.

3. The method of claim 1, wherein the sensing, using the one or more electrodes, the bioelectrical brain activity of the brain of the patient comprises continuously sensing, using the one or more electrodes, the bioelectrical brain activity of the brain of the patient, and
wherein the identifying the window of the stimulation parameter having the first threshold as the lower boundary and the after-discharge threshold as the upper boundary based on the sensed bioelectrical brain activity comprises continuously identifying the after-discharge threshold as the upper boundary based on the sensed bioelectrical brain activity such that the upper boundary is continuously adjusted.

4. The method of claim 1, wherein the electrical stimulation comprises a first electrical stimulation, wherein the bioelectrical brain activity comprises a first bioelectrical brain activity, and wherein the bioelectrical response comprises a first bioelectrical response, the method further comprising:
subsequently controlling the stimulation circuitry to deliver a second electrical stimulation to the brain at the plurality of different levels of the stimulation parameter;
sensing, using the one or more electrodes, a second bioelectrical brain activity, wherein sensing the second bioelectrical brain activity of the brain comprises sensing a second bioelectrical response of the brain to the delivery of the second electrical stimulation at each of the plurality of different levels of the stimulation parameter; and
adjusting the after-discharge threshold as the upper boundary based on the sensed second bioelectrical brain activity.

5. The method of claim 1, wherein the first threshold comprises a therapeutic effect threshold at which a therapeutic effect is produced by the stimulation.

6. The method of claim 1, further comprising determining a frequency domain characteristic of the sensed bioelectrical brain activity, wherein identifying the window of the stimulation parameter having the first threshold as the lower boundary and the after-discharge threshold as the upper boundary based on the sensed bioelectrical brain activity comprises identifying the window of the stimulation parameter having the first threshold as the lower boundary and the after-discharge threshold as the upper boundary based on the determined frequency domain characteristic.

7. The method of claim 6, wherein the frequency domain characteristic of the sensed bioelectrical brain activity comprises at least one of a power level in one or more frequency bands of the sensed bioelectrical brain activity or a ratio of power levels in at least two frequency bands of the sensed bioelectrical brain activity.

8. The method of claim 1, wherein the sensed bioelectrical brain activity comprises sensed local field potential signals.

9. The method of claim 1, wherein the first threshold comprises a suppression threshold.

10. The method of claim 1, wherein the stimulation parameter is a stimulation amplitude.

11. The method of claim 1, further comprising controlling the stimulation circuitry to deliver the therapy to the brain of the patient with the set therapy level of the stimulation parameter.

12. The method of claim 1, wherein the electrical stimulation comprises a first electrical stimulation, wherein the bioelectrical brain activity comprises a first bioelectrical brain activity, and wherein the bioelectrical response comprises a first bioelectrical response, the method further comprising:
controlling the stimulation circuitry to deliver the therapy to the brain of the patient with the set therapy level of the stimulation parameter;
subsequently controlling the stimulation circuitry to deliver a second electrical stimulation to the brain at the plurality of different levels of the stimulation parameter;
sensing, using the one or more electrodes, a second bioelectrical brain activity, wherein sensing the second bioelectrical brain activity of the brain comprises sensing a second bioelectrical response of the brain to the delivery of the second electrical stimulation at each of the plurality of different levels of the stimulation parameter, wherein sensing the bioelectrical response comprises sensing another after-discharge episode resulting from the delivery of the second electrical stimulation at at least one level of the plurality of different levels of the stimulation parameter; and
adjusting the after-discharge threshold as the upper boundary of the window of the stimulation parameter based on the at least one level of the plurality of different levels of the stimulation parameter that resulted in the sensed another after-discharge episode.

13. The method of claim 12, further comprising:
resetting the therapy level of the stimulation parameter for therapy delivery to the brain based on the adjusted after-discharge threshold; and
controlling the stimulation circuitry to deliver the therapy to the brain of the patient with the reset therapy level of the stimulation parameter.

14. A system comprising:
one or more electrodes;
stimulation circuitry configured to generate electrical stimulation; and
control circuitry configured to:
control the stimulation circuitry to deliver the electrical stimulation to a brain at a plurality of different levels of a stimulation parameter;
sense, using the one or more electrodes, bioelectrical brain activity, wherein sensing the bioelectrical brain activity of the brain comprises sensing a bioelectrical response of the brain to the delivery of the electrical stimulation at each of the plurality of different levels of the stimulation parameter, wherein the control circuitry is configured to sense an after-discharge episode resulting from the delivery of the electrical stimulation at at least one level of the plurality of different levels of the stimulation parameters;
identify a window of the stimulation parameter having a first threshold as a lower boundary and an after-discharge threshold as an upper boundary based on the sensed bioelectrical brain activity, wherein the control circuitry is configured to determine the first threshold and the after-discharge threshold of the stimulation parameter based on the sensed bioelectrical activity, wherein the control circuitry is configured to determine the after discharge threshold based on the at least one level of the plurality of different levels of the stimulation parameter that resulted in the sensed after-discharge episode; and set a level of the stimulation parameter for therapy delivery to the brain based on the window.

15. The system of claim 14, wherein the control circuitry is configured to periodically sense, using the one or more electrodes, the bioelectrical brain activity of the brain of the patient, and periodically identify the after-discharge threshold as the upper boundary based on the sensed bioelectrical brain activity such that the upper boundary is periodically adjusted.

16. The system of claim 14, wherein the control circuitry is configured to continuously sense, using the one or more electrodes, the bioelectrical brain activity of the brain of the patient, and continuously identify the after-discharge threshold as the upper boundary based on the sensed bioelectrical brain activity such that the upper boundary is continuously adjusted.

17. The system of claim 14, wherein the electrical stimulation comprises a first electrical stimulation, wherein the bioelectrical brain activity comprises a first bioelectrical brain activity, wherein the bioelectrical response comprises a first bioelectrical response, and wherein the control circuitry is configured to:
   subsequently control the stimulation circuitry to deliver a second electrical stimulation to the brain at the plurality of different levels of the stimulation parameter;
   sense, using the one or more electrodes, a second bioelectrical brain activity, wherein sensing the second bioelectrical brain activity of the brain comprises sensing a second bioelectrical response of the brain to the delivery of the second electrical stimulation at each of the plurality of different levels of the stimulation parameter; and
   adjust the after-discharge threshold as the upper boundary based on the sensed second bioelectrical brain activity.

18. The system of claim 14, wherein the first threshold comprises a therapeutic effect threshold at which a therapeutic effect is produced by the stimulation.

19. The system of claim 14, wherein the control circuitry is configured to determine a frequency domain characteristic of the sensed bioelectrical brain activity, and identify the window of the stimulation parameter having the first threshold as the lower boundary and the after-discharge threshold as the upper boundary based on the determined frequency domain characteristic.

20. The system of claim 19, wherein the frequency domain characteristic of the sensed bioelectrical brain activity comprises at least one of a power level in one or more frequency bands of the sensed bioelectrical brain activity or a ratio of power levels in at least two frequency bands of the sensed bioelectrical brain activity.

21. The system of claim 14, wherein the sensed bioelectrical brain activity comprises sensed local field potential signals.

22. The system of claim 14, wherein the first threshold comprises a suppression threshold.

23. The system of claim 14, wherein the stimulation parameter is a stimulation amplitude.

24. The system of claim 14, wherein the control circuitry is configured to control the stimulation circuitry to deliver the therapy to the brain of the patient with the set therapy level of the stimulation parameter.

25. The system of claim 14, wherein the electrical stimulation comprises a first electrical stimulation, wherein the bioelectrical brain activity comprises a first bioelectrical brain activity, wherein the bioelectrical response comprises a first bioelectrical response, and wherein the control circuitry is configured to:
   control the stimulation circuitry to deliver the therapy to the brain of the patient with the set therapy level of the stimulation parameter
   subsequently control the stimulation circuitry to deliver a second electrical stimulation to the brain at the plurality of different levels of the stimulation parameter;
   sense, using the one or more electrodes, a second bioelectrical brain activity, wherein sensing the second bioelectrical brain activity of the brain comprises sensing a second bioelectrical response of the brain to the delivery of the second electrical stimulation at each of the plurality of different levels of the stimulation parameter, wherein the control circuitry is configured to sense another after-discharge episode resulting from the delivery of the second electrical stimulation at at least one level of the plurality of different levels of the stimulation parameters; and
   adjust the after-discharge threshold as the upper boundary of the window of the stimulation parameter based on the at least one level of the plurality of different levels of the stimulation parameter that resulted in the sensed another after-discharge episode.

26. The system of claim 25, wherein the control circuitry is configured to:
   reset the therapy level of the stimulation parameter for therapy delivery to the brain based on the adjusted after-discharge threshold; and
   control the stimulation circuitry to deliver the therapy to the brain of the patient with the reset therapy level of the stimulation parameter.

* * * * *